(12) United States Patent
Caldwell et al.

(10) Patent No.: US 7,705,028 B2
(45) Date of Patent: Apr. 27, 2010

(54) FARNESOID X RECEPTOR AGONISTS

(75) Inventors: Richard Caldwell, Durham, NC (US); David Norman Deaton, Durham, NC (US); Robert Blout McFayden, Durham, NC (US); Frank Navas, III, Durham, NC (US); Paul Kenneth Spearing, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 239 days.

(21) Appl. No.: 11/609,914

(22) Filed: Dec. 13, 2006

(65) Prior Publication Data

US 2008/0167356 A1    Jul. 10, 2008

Related U.S. Application Data

(60) Provisional application No. 60/751,597, filed on Dec. 19, 2005.

(51) Int. Cl.
*A61K 31/42* (2006.01)
*C07D 261/06* (2006.01)

(52) U.S. Cl. ........................... 514/378; 548/247
(58) Field of Classification Search ............. 514/378; 548/247
See application file for complete search history.

(56) References Cited

U.S. PATENT DOCUMENTS

| 6,639,078 B1 | 10/2003 | Haffner et al. |
| 7,319,109 B2 * | 1/2008 | Boggs et al. ............. 514/378 |
| 2004/0048316 A1 | 3/2004 | Haffner et al. |
| 2004/0127443 A1 | 7/2004 | Pershadsingh |
| 2004/0198980 A1 | 10/2004 | Haffner et al. |
| 2006/0258725 A1 | 11/2006 | Boggs et al. |

FOREIGN PATENT DOCUMENTS

| EP | 1285914 | 2/2003 |
| WO | 98/43953 | 10/1998 |
| WO | 03/015771 | 2/2003 |
| WO | 03/016280 | 2/2003 |
| WO | 03/087140 | 10/2003 |
| WO | WO 2004/048349 | 6/2004 |
| WO | WO 2007/072751 | 8/2007 |

OTHER PUBLICATIONS

Vippagunta, et al., Crystalline solids, 2001, Advanced Drug Delivery Reviews, 48, pp. 3 and 18.*
Chenard, B.L., et al., A Unified Approach to Systematic Isosteric Substitution for Acidic Groups and Application to NMDA Antagonists Related to 2-Amino-7-phosphonoheptanoate, *J. Med. Chem.*; 33, 1077-1083 (1990).
Weller, H.N., et al., Synthesis of N-Alkyl-1,2,4-Oxadiazinones as Angiotensin-II ($AT_1$) Receptor Antagonists, *Heterocycles* 36(5), 1027-1038 (1993).
Ellingboe, J.W., et al., Antihyperglycemic Activity of Novel Naphthalenyl 3*H*-1,2,3,5-Oxathiadiazole 2-Oxides, *J. Med. Chem.*; 36, 2485-2493 (1993).
Kees, K.L., et al., Studies on New Acidic Azoles as Glucose-Lowering Agents in Obese, Diabetic db/db Mice, *J. Med. Chem.*; 38, 617-628 (1995).
Ornstein, P.L., et al., Structure-Activity Studies of 6-Substituted Decahydroisoquinoline-3-carboxylic Acid AMPA Receptor Antagonists, 2. Effects of Distal Acid Bioisosteric Substitution, Absolute Stereochemical Preferences, and in Vivo Activity, *J. Med. Chem.*; 39, 2232-2244 (1996).
Kohara, Yasuhisa, et al., Synthesis and Angiotensin II Receptor Antagonistic Activities of Benzimidazole Derivatives Bearing Acidic Heterocycles as Novel Tetrazole Bioisosteres, *J. Med. Chem.*; 39, 5228-5235 (1996).
Matzen, Lisa, et al., AMPA Receptor Agonists: Synthesis, Protolytic Properties, and Pharmacology of 3-Isothiazolol Bioisosteres of Glutamic Acid, *J. Med. Chem.*; 40, 520-527 (1997).

* cited by examiner

*Primary Examiner*—Kamal A Saeed
*Assistant Examiner*—Kristin Bianchi
(74) *Attorney, Agent, or Firm*—Robert (Steve) Thomas

(57) ABSTRACT

The present invention provides novel substituted isoxazole compounds, pharmaceutical compositions, therapeutic uses and processes for preparing the same.

18 Claims, No Drawings

FARNESOID X RECEPTOR AGONISTS

CROSS-REFERENCE TO RELATED APPLICATION

The instant application claims priority to U.S. Provisional Patent Application Ser. No. 60/751,597, filed 19 Dec. 2005.

BACKGROUND OF THE INVENTION

The present invention relates to farnesoid X receptors (FXR). More particularly, the present invention relates to compounds useful as agonists for FXR, pharmaceutical formulations comprising such compounds, and therapeutic use of the same.

FXR is a member of the nuclear receptor class of ligand-activated transcription factors. Physiological concentrations of bile acids bind and activate FXR. [Parks, D. J., et al. 1999 Science 284:1365-1368; Makishima, M., et al. 1999 Science 284:1362-1365] Bile acids are amphipathic molecules that form micelles and emulsify dietary lipids. This property also makes bile acids cytotoxic if sufficient concentrations are achieved and thus mechanisms have evolved to ensure bile acid concentrations are tightly regulated. FXR plays a key role in regulating bile acid homeostasis. [Makishima, M. 2005 J Pharmacol Sci 97:177-183; Kuipers, F. et al. 2004 Rev Endocrine Metab Disorders 5:319-326]

FXR is expressed in liver, intestine, kidney, and adrenal. [Kuipers, F. et al. 2004 Rev Endocrine Metab Disorders 5:319-326] FXR target genes in hepatocytes include SHP which encodes small heterodimer partner, an atypical nuclear receptor that represses transcription of genes such as CYP7A1 (encoding cholesterol 7α-hydroxylase), the first and rate limiting step in the conversion of cholesterol to bile acid, CYP8B1 (encoding sterol 12α-hydroxylase) which controls the hydrophobicity of the bile pool and NTCP (encoding the sodium/taurocholate co-transporting polypeptide) that imports bile acids from the portal and systemic circulation into the hepatocyte. [Goodwin, B., et al. 2000 Mol. Cell. 6:517-526; del Castillo-Olivares, A., et al 2001 Nucleic Acids Res. 29:4035-4042; Denson, L A, et al. 2001 Gastroenterology 121(1):140-147] Other FXR target genes that are induced in liver include the canalicular transporter BSEP (encoding the bile salt export pump) that transports bile acids from the hepatocyte into the bile, multi-drug resistance (MDR3) (encoding the canalicular phospholipid flippase) that transports phospholipids from the hepatocyte into the bile and MRP2 (encoding multidrug resistance-related protein-2) that transports conjugated bilirubin, glutathione and glutathione conjugates into bile. Ananthanarayanan, M., et al. 2001 J. Biol. Chem. 276:28857-28865; Huang, L et al., 2003 J. Biol. Chem. 278(51):51085-51090; Kast, H. R., et al. 2002 J. Biol. Chem. 277:2908-2915.

In the intestine FXR also induces expression of SHP which represses transcription of the ASBT gene which encodes the high affinity apical sodium dependent bile acid transporter that moves bile acids from the intestinal lumen into the enterocyte as part of the enterohepatic recycling of bile acids. [Li, H., et al. 2005 μm. J. Physiol. Gastrointest. Liver Physiol. 288(1)G60-6] IBABP gene expression is also induced by FXR agonists in the enterocyte. [Grober, J. et al., 1999 J. Biol. Chem. 274(42):29749-54] The function of this ileal bile acid binding protein remains under investigation.

Cholestasis is a condition of reduced or arrested bile flow. Unresolved cholestasis leads to liver damage such as that seen in primary biliary cirrhosis (PBC) and primary sclerosing cholangitis (PSC), two cholestatic liver diseases. FXR agonists have been shown to protect the liver in rodent models of cholestatic liver disease. [Liu, Y. et al. 2003 JCI 112(11): 1678-1687; Fiorucci, S., et al JPET 313(2):604-612; Pelicciari, R., et al 2002 J. Med. Chem. 45(17):3569-3572]

FXR is also expressed in hepatic stellate cells (HSC) which play a role in deposition of extracellular matrix during the fibrotic process. Treatment of cultured HSCs with the FXR agonist 6-ethyl-chenodeoxycholic acid (6EtCDCA) results in decreased expression of fibrotic markers such as α-smooth muscle actin and α1(I)collagen. 6EtCDCA has also been reported to prevent development and promote resolution of hepatic fibrosis in multiple rodent models of this disease. Fiorucci, S., et al. 2004 Gastroenterology 127(5):1497-1512; Fiorucci, S., et al. 2005 JPET 314(2):584-595. According to Fiorucci et al., this anti-fibrotic effect is due to SHP inactivation of Jun and subsequent repression of tissue inhibitor of metalloproteinase 1 (TIMP1) via the AP1 binding site on the TIMP1 promoter.

Recently, S. Kliewer presented data at the Digestive Diseases Week (DDW) Conference (2005) organized by the American Association for the study of Liver Disease (AASLD) showing that activation of FXR by the agonist GW4064 resulted in improved mucosal barrier and decreased bacterial overgrowth in a bile duct-ligated mouse model of cholestasis and intestinal bacterial overgrowth. Dr. Kliewer showed data indicating decreased translocation of bacteria to mesenteric lymph nodes in mice treated with GW4064. This effect of GW4064 was lost in FXR null mice.

The FXR agonist GW4064, when administered to mice on a lithogenic diet, prevented the formation of cholesterol crystals in the bile. This effect of the compound was lost in FXR null mice. Moschetta, A., et al 2004 Nat. Med. 10:1352-1358.

SUMMARY OF THE INVENTION

As a first aspect, the present invention provides compounds of formula (I):

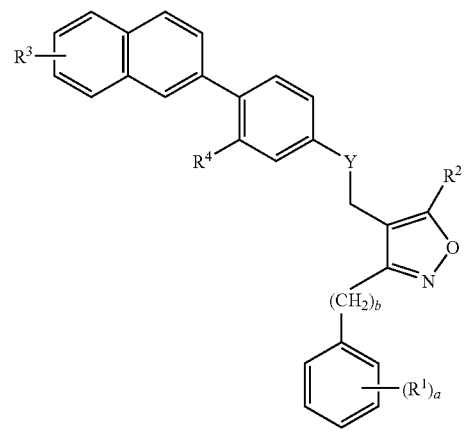

wherein:
a is 1, 2, 3, 4 or 5;
each $R^1$ is the same or different and is independently selected from the group consisting of halo, alkyl, alkenyl, —O—$CF_3$, —$OR^6$, —$S(O)_fR^6$, —$NR^6R^7$, —$R^5OR^6$, —$R^5S(O)_fR^6$, —$R^5NR^6R^7$ and cyano;
b is 0, 1, 2 or 3;
$R^2$ is selected from the group consisting of alkyl, alkenyl, $C_{3-6}$cycloalkyl, $C_{3-6}$cycloalkenyl, —$R^5OR^6$, —$R^5NR^6R^7$, and cyano;
Y is —O—, —S— or —N($R^3$)—;
$R^3$ is an acid, amide, ester or acid-equivalent group;
$R^4$ is H, halo, alkyl or haloalkyl;

each $R^5$ is the same or different and is independently selected from the group consisting of alkylene and alkenylene;
each $R^6$ and $R^7$ are the same or different and are each independently selected from the group consisting of H, alkyl, alkenyl, $C_{3-6}$cycloalkyl and $C_{3-6}$cyclolalkenyl; and
f is 0, 1 or 2;
each $R^8$ is the same or different and is independently H or alkyl;

or a pharmaceutically acceptable salt or solvate thereof.

In a second aspect, the present invention provides a composition comprising a compound of formula (I). The composition may further comprise a pharmaceutically acceptable carrier or diluent.

In a third aspect, the present invention provides a method for the treatment of a condition mediated by FXR in a subject in need thereof. The method comprises administering to the subject a therapeutically effective amount of a compound of formula (I).

In a fourth aspect, the present invention provides a method for the treatment of cholestatic liver disease in a subject in need thereof. The method comprises administering to the subject a therapeutically effective amount of a compound of formula (I).

In a fifth aspect, the present invention provides a method for the treatment of organ fibrosis in a subject in need thereof. The method comprises administering to the subject a therapeutically effective amount of a compound of formula (I).

In a sixth aspect, the present invention provides a method for the treatment of liver fibrosis in a subject in need thereof. The method comprises administering to the subject a therapeutically effective amount of a compound of formula (I).

In a seventh aspect, the present invention provides a method for the treatment of diabetes mellitus in a subject in need thereof. The method comprises administering to the subject a therapeutically effective amount of a compound of formula (I).

In an eighth aspect, the present invention provides a method for the treatment of metabolic syndrome in a subject in need thereof. The method comprises administering to the subject a therapeutically effective amount of a compound of formula (I).

In a ninth aspect, the present invention provides a method for the treatment of obesity in a subject in need thereof. The method comprises administering to the subject a therapeutically effective amount of a compound of formula (I).

In a tenth aspect, the present invention provides a process for preparing a compound of formula (I). The process comprises the steps of:
a) reacting a compound of formula (VIII)

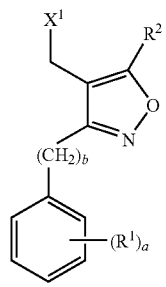

VIII wherein:
$X^1$ is chloro, iodo, bromo, triflate, tosylate, nosylate, besylate or mesylate, (preferably chloro); and
all other variables are as defined above with a compound of formula (IX)

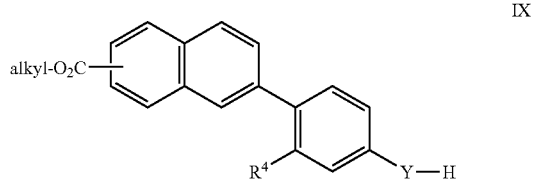

IX to prepare a compound of formula (I-A);

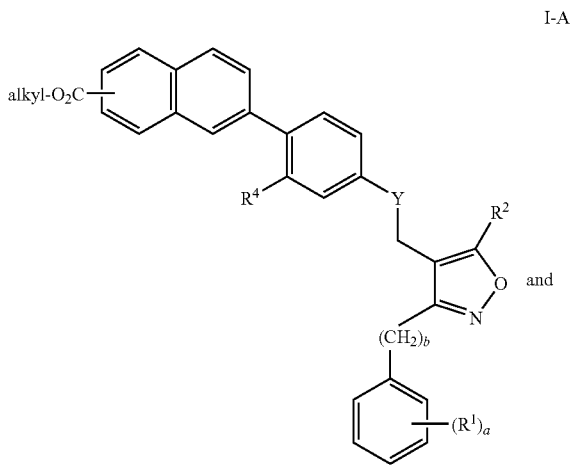

I-A and b) optionally converting the compound of formula (I-A) into a different compound of formula (I).

In another aspect, the present invention provides another process for preparing a compound of formula (I). This process comprises the steps of:
a) reacting a compound of formula (VIII-B)

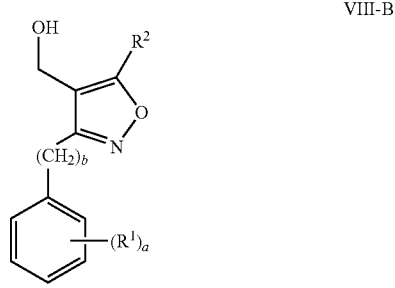

VIII-B with a compound of formula (IX)

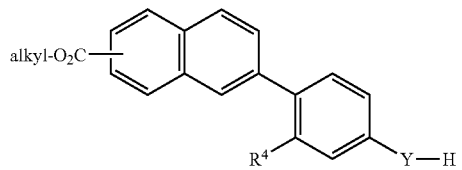

IX to prepare a compound of formula (I-A);

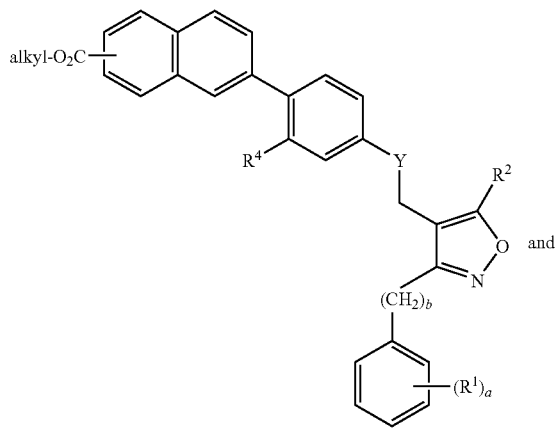

b) optionally converting the compound of formula (I-A) into a different compound of formula (I).

In another aspect, the present invention provides a compound of formula (I) for use in therapy. The present invention also provides a compound of formula (I) for use in the treatment of a condition mediated by FXR in a subject; a compound of formula (I) for use in the treatment of cholestatic liver disease in a subject; a compound of formula (I) for use in the treatment of organ fibrosis in a subject; a compound of formula (I) for use in the treatment of liver fibrosis in a subject; a compound of formula (I) for use in the treatment of diabetes mellitus in a subject; a compound of formula (I) for use in the treatment of metabolic syndrome in a subject; and a compound of formula (I) for use in the treatment of obesity in a subject.

In another aspect, the present invention provides the use of a compound of formula (I) for the preparation of a medicament for the treatment of a condition mediated by FXR in a subject; the use of a compound of formula (I) for the preparation of a medicament for the treatment of cholestatic liver disease in a subject; the use of a compound of formula (I) for the preparation of a medicament for the treatment of organ fibrosis in a subject; the use of a compound of formula (I) for the preparation of a medicament for the treatment of liver fibrosis in a subject; the use of a compound of formula (I) for the preparation of a medicament for the treatment of diabetes mellitus in a subject; the use of a compound of formula (I) for the preparation of a medicament for the treatment of metabolic syndrome in a subject; and the use of a compound of formula (I) for the preparation of a medicament for the treatment of obesity.

In another aspect, the present invention provides a pharmaceutical composition comprising a compound of formula (I) for use in the treatment of a condition mediated by FXR.

Further aspects of the present invention are described in the description of particular embodiments, examples, and claims which follow.

DETAILED DESCRIPTION OF THE PREFERRED EMBODIMENTS

As used herein, "a compound of the invention" or "a compound of formula (I)" means a compound of formula (I) or a pharmaceutically acceptable salt or solvate thereof. Similarly, with respect to isolatable intermediates such as for example, compounds of formula (V), (VI), (VIII), (VIII-B) and (IX), the phrase "a compound of formula (number)" means a compound having that formula or a pharmaceutically acceptable salt or solvate thereof.

As used herein, the term "alkyl" refers to aliphatic straight or branched saturated hydrocarbon chains containing 1-8 carbon atoms. Examples of "alkyl" groups as used herein include but are not limited to methyl, ethyl, n-propyl, isopropyl, n-butyl, isobutyl, t-butyl, pentyl, hexyl, octyl and the like. The term "haloalkyl" refers to halo substituted alkyl, including trihaloalkyl, such as trifluoromethyl and trifluoroethyl among others.

The term "alkylene" refers to a straight or branched alkyl bridge, i.e., the group -alkyl-, wherein alkyl is as defined above.

As used herein, the term "halo" refers to any halogen atom. i.e., fluorine, chlorine, bromine or iodine.

As used herein, the term "alkenyl" refers to an aliphatic straight or branched unsaturated hydrocarbon chain containing 2-8 carbon atoms and at least one and up to three carbon-carbon double bonds. Examples of "alkenyl" groups as used herein include but are not limited to ethenyl and propenyl.

The term "alkenylene" refers to a straight or branched alkenyl bridge, i.e., the group -alkenyl-, wherein alkenyl is as defined above.

As used herein, the term "cycloalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. For example, the cycloalkyl may optionally be substituted on any available carbon with one or more substituents selected from the group consisting of halo, alkyl, haloalkyl, alkenyl, —OH, —O-alkyl, —NH$_2$, —NH(alkyl)-N(alkyl)$_2$, —CN, —NO$_2$ and —N$_3$. As will be appreciated by those skilled in the art, the number of possible substituents on the cycloalkyl ring will depend upon the size of ring. Particular cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and from 1 to 3 carbon-carbon double bonds. "Cycloalkenyl" includes by way of example cyclopropenyl, cyclobutenyl, cyclopentenyl, cyclohexenyl, cycloheptenyl and cyclooctenyl. "Cycloalkenyl" also includes substituted cycloalkyl. For example, the cycloalkenyl may optionally be substituted on any available carbon with one or more substituents selected from the group consisting of halo, alkyl, haloalkyl, alkenyl, —OH, —O-alkyl, —NH$_2$, —NH(alkyl)-N(alkyl)$_2$, —CN, —NO$_2$ and —N$_3$. As will be appreciated by those skilled in the art, the number of possible substituents on the cycloalkenyl ring will depend upon the size of ring. Particular cycloalkenyl groups include $C_{3-6}$cycloalkenyl and substituted $C_{3-6}$cycloalkenyl.

As used herein, the term "optionally" means that the subsequently described event(s) may or may not occur, and includes both event(s) that occur and events that do not occur.

As used herein, the term "treatment" includes the prevention of occurrence of symptoms of the condition or disease in the subject, the prevention of recurrence of symptoms of the condition or disease in the subject, the delay of recurrence of symptoms of the condition or disease in the subject, the decrease in severity or frequency of outward symptoms of the condition or disease in the subject, slowing or eliminating the progression of the condition and the partial or total elimination of symptoms of the disease or condition in the subject.

The present invention relates to compounds of formula (I):

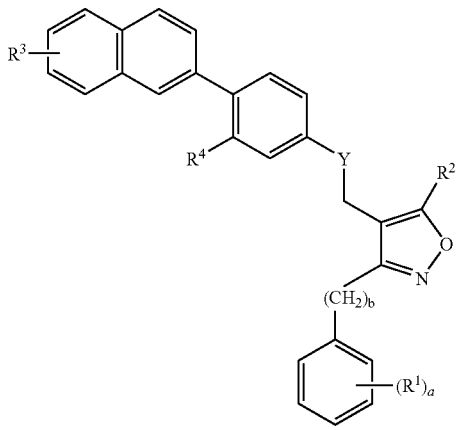

wherein:
a is 1, 2, 3, 4 or 5;
each $R^1$ is the same or different and is independently selected from the group consisting of halo, alkyl, alkenyl, —$OR^6$, —$S(O)_fR^6$, —$NR^6R^7$, —$R^5OR^6$, —$R^5S(O)_fR^6$, —$R^5NR^6R^7$ and cyano;
b is 0, 1, 2 or 3;
$R^2$ is selected from the group consisting of alkyl, alkenyl, $C_{3-6}$cycloalkyl, $C_{3-6}$cycloalkenyl, —$R^5OR^6$, —$R^5NR^6R^7$ and cyano;
Y is —O—, —S— or —$N(R^8)$—;
$R^3$ is an acid, amide, ester or acid-equivalent group;
$R^4$ is H, halo, alkyl or haloalkyl;
each $R^5$ is the same or different and is independently selected from the group consisting of alkylene and alkenylene;
each $R^6$ and $R^7$ are the same or different and are each independently selected from the group consisting of H, alkyl, alkenyl, $C_{3-6}$cycloalkyl and $C_{3-6}$cyclolalkenyl; and
f is 0, 1 or 2;
each $R^8$ is the same or different and is independently H or alkyl;

or a pharmaceutically acceptable salt or solvate thereof.

In the compounds of formula (I) the group(s) $R^1$ may be bonded in the ortho, meta or para positions. In one embodiment, the compound of formula (I) is defined wherein a is 1, 2, 3, 4 or 5. In one particular embodiment, a is 1 or 2. In one particular embodiment, a is 2. In one particular embodiment, a is 2 and each $R^1$ is in the ortho position.

In one embodiment, the compounds of formula (I) are defined wherein each $R^1$ is the same or different and is independently selected from the group consisting of halo, alkyl, and —$OR^6$, or any subset thereof. In a particular embodiment, each $R^1$ is the same or different and is independently selected from the group consisting of halo, alkyl, —O-alkyl, —O-haloalkyl, or any subset thereof. In a particular embodiment, each $R^1$ is the same or different and is independently selected from the group consisting of halo and —$OR^6$, or any subset thereof. In a particular embodiment, each $R^1$ is the same or different and is halo. More specifically, in one embodiment, each $R^1$ is the same or different and is independently selected from the group consisting of Cl, F, methyl, and —O—$CF_3$, or any subset thereof. More specifically, in one embodiment, each $R^1$ is Cl. In another embodiment, each $R^1$ is methyl.

In one embodiment, the compounds of formula (I) are defined wherein b is 0 or 2. In one particular embodiment, b is 0. In one particular embodiment, b is 2.

In one embodiment of the present invention, $R^2$ is selected from the group consisting of alkyl and $C_{3-6}$cycloalkyl. In one particular embodiment, $R^2$ is alkyl. More specifically, particular groups defining $R^2$ are selected from the group consisting of methyl, ethyl, isopropyl, cyclopropyl, and cyclobutyl, or any subset thereof. In one particular embodiment, $R^2$ is isopropyl.

In one embodiment, the compounds of formula (I) are defined wherein Y is —O—. In another particular embodiment, the compounds of formula (I) are defined wherein Y is —$N(R^5)$—. In one embodiment, Y is —$N(R^5)$—, wherein $R^5$ is selected from the group consisting of H and methyl.

$R^3$ is an acid, amide, ester or acid-equivalent group. The term "acid" in the definition of $R^3$ refers to a group —$C(O)_2H$. As will be appreciated by those skilled in the art, pharmaceutically acceptable salts of compounds of formula (I) wherein $R^3$ is an acid refers to salts of such acids, e.g., —$C(O)_2^-Na^+$ or —$C(O)_2^-K^+$. The term "amide" in the definition of $R^3$ refers to a group —$C(O)_2NR^aR^b$, wherein $R^a$ and $R^b$ are each independently selected from H, alkyl, alkenyl, cycloalkyl and cycloalkenyl or $R^a$ and $R^b$ together with the N atom to which they are attached form a 3-8 membered heterocyclic ring containing 1 N. The term "ester" in the definition of $R^3$ refers to a group —$C(O)_2R^c$, wherein $R^c$ is selected from alkyl, alkenyl, cycloalkyl and cycloalkenyl. As used herein, the term "acid-equivalent group" means a functional group with an acidic proton that may take the place of a carboxylic acid in a biological system. Examples of acid-equivalent groups according to the present invention include but are not limited to nitrile, tetrazole, 1,2,4-oxadiazolidine-3,5-diones, 3(2H)-isoxazolones, 1,2,4-oxadiazol-5(2H)-ones, 3H-1,2,3,5-oxathiadiazole 2-oxides.

In one embodiment of the present invention, $R^3$ is an acid or acid-equivalent group. In one particular embodiment, $R^3$ is an acid.

In one embodiment of the present invention, $R^4$ is selected from the group consisting of H or halo. In one particular embodiment, $R^4$ is H.

The present invention contemplates and includes all combinations and subsets of the particular groups defined above.

Specific examples of particular compounds of the present invention are selected from the group consisting of:
6-[4-({[3-(2,6-Dichlorophenyl)-5-(1-methylethyl)-4-isoxazolyl]methyl}oxy)phenyl]-1-naphthoic acid sodium salt;
6-[4-({[3-(2,6-Dichlorophenyl)-5-(1-methylethyl)-4-isoxazolyl]methyl}oxy)phenyl]-1-naphthalenecarboxylic acid;
6-[2-Chloro-4-({[3-(2,6-dichlorophenyl)-5-(1-methylethyl)-4-isoxazolyl]methyl}oxy)phenyl]-1-naphthalenecarboxylic acid;
6-[4-({[5-cyclobutyl-3-(2,6-dichlorophenyl)-4-isoxazolyl]methyl}oxy)phenyl]-1-naphthalenecarboxylic acid;
6-[4-({[3-[(2,6-dichlorophenyl)methyl]-5-(1-methylethyl)-4-isoxazolyl]methyl}oxy)phenyl]-1-naphthalenecarboxylic acid;
6-[4-({[3-[2-(2,6-dichlorophenyl)ethyl]-5-(1-methylethyl)-4-isoxazolyl]methyl}oxy)phenyl]-1-naphthalenecarboxylic acid;
6-(4-{[3-(2,6-dichlorophenyl)-5-isopropylisoxazol-4-yl]methoxy}phenyl)-2-naphthoic acid;
Methyl 6-[4-({[3-[2-(2,6-dichlorophenyl)ethyl]-5-(1-methylethyl)-4-isoxazolyl]methyl}oxy)phenyl]-2-naphthalenecarboxylate;
7-[4-({[3-(2,6-dichlorophenyl)-5-(1-methylethyl)-4-isoxazolyl]methyl}oxy)phenyl]-2-naphthalenecarboxylic acid;
7-[4-({[3-[2-(2,6-dichlorophenyl)ethyl]-5-(1-methylethyl)-4-isoxazolyl]methyl}oxy)phenyl]-2-naphthalenecarboxylic acid;

7-[4-({[3-(2,6-dichlorophenyl)-5-(1-methylethyl)-4-isoxazolyl]methyl}oxy)phenyl]-1-naphthalenecarboxylic acid;

7-[4-({[3-[2-(2,6-dichlorophenyl)ethyl]-5-(1-methylethyl)-4-isoxazolyl]methyl}oxy)phenyl]-1-naphthalenecarboxylic acid;

6-[4-({[3-(2,6-dichlorophenyl)-5-(1-methylethyl)-4-isoxazolyl]methyl}oxy)phenyl]-1-naphthalenecarboxamide;

6-[4-({[3-(2,6-dichlorophenyl)-5-(1-methylethyl)-4-isoxazolyl]methyl}oxy)phenyl]-1-naphthalenecarbonitrile;

5-{6-[4-({[3-(2,6-dichlorophenyl)-5-(1-methylethyl)-4-isoxazolyl]methyl}oxy)phenyl]-1-naphthalenyl}-1H-tetrazole;

6-[4-({[3-(2,6-Dichlorophenyl)-5-(1-methylethyl)-4-isoxazolyl]methyl}oxy)phenyl]-1-naphthoic acid tris(hydroxymethyl)aminomethane salt;

and pharmaceutically acceptable salts or solvates thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted.

Suitable pharmaceutically acceptable salts according to the present invention will be readily determined by one skilled in the art and will include, for example, salts prepared from inorganic bases such as lithium hydroxide, sodium hydroxide, potassium hydroxide, lithium hydride, sodium hydride, potassium hydride, lithium carbonate, lithium hydrogen carbonate, sodium carbonate, sodium hydrogen carbonate, potassium carbonate, potassium hydrogen carbonate, as well as potassium tert-butoxide and organic bases such as diethyl amine, lysine, arginine, choline, tris(hydroxymethyl)aminomethane (tromethamine), triethanolamine, diethanolamine, and ethanolamine. In one embodiment, the compounds of formula (I) are in the form of the sodium salt.

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" refers to a crystal form containing the compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

Processes for preparing pharmaceutically acceptable salts and solvates of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts and/or solvates of the compound. Those terms as applied to any intermediate employed in the process of preparing compounds of formula (I) have the same meanings as noted above with respect to compounds of formula (I).

Processes for preparing pharmaceutically acceptable salts and solvates of such intermediates are known in the art and are analogous to the process for preparing pharmaceutically acceptable salts and solvates of the compounds of formula (I).

In one embodiment, the compounds of formula (I) are FXR agonists. As used herein, the term "FXR agonist" refers to compounds which exhibit a $pEC_{50}$ greater than 4 in the FXR Cofactor Recruitment Assay described below. More particularly, FXR agonists are compounds which exhibit a $pEC_{50}$ greater than 5 in the FXR Cofactor Recruitment Assay described below.

Compounds of formula (I) are useful in therapy in subjects such as mammals, and particularly humans. In particular, the compounds of formula (I) are useful in the treatment of a condition mediated by FXR in a subject such as a mammal, particularly a human. Conditions mediated by FXR include but are not limited to cardiovascular diseases; disease states and complications related to dyslipidemia (C. Sinal, Cell 102: 731-744 (2000)); disorders of the liver such as cholestatic liver disease (Liu, Y. et al., J. Clin. Invest. 112:1678-1687 (2003)) and cholesterol gallstone disease (Moschetta, A., et al., Nat. Med. 10:1352-1358 (2004)); organ fibrosis (Fiorucci, S, et al. Gastroenterology 127:1497-1512 (2004) and Fiorucci, et al., JPET 314(2):584-595 (2005)) including liver fibrosis (Fiorucci, S, et al. Gastroenterology 127:1497-1512 (2004)); diabetes mellitus (Duran-Sandoval, D. et al, Diabetes 53:890-898 (2004); Bilz, S. et al., Am. J. Physiol Endocrinol. Metab., (Epub ahead of print, 2005); Nozawa, H, Biochem. Biophys. Res. Commun., 336:754-761 (2005); Duran-Sandoval, D., et al., Biochimie, 87:93-98 (2005); Claudel, T., et al., Arterioscler. Thromb. Vasc. Biol., 25:2020-2030 (2005); Duran-Sandoval, D., et al., J. Biol. Chem., 280: 29971-29979 (2005); Savkur, R. S., et al., Biochem. Biophys. Res. Commun., 329:391-396 (2005)); metabolic syndrome; obesity and depression.

Compounds of formula (I) are useful in the treatment of cardiovascular disease in a subject such as a mammal, particularly a human. For example, the compounds of formula (I) are useful in the treatment of atherosclerosis, hypercholesterolemia or hyperlipidemia in a subject in need thereof.

Compounds of formula (I) are also useful for the treatment of disease states and complications related to dyslipidemia. The compounds of the present invention increase the flow of bile acid. Increased flow of bile acids improves the flux of bile acids from the liver to the intestine. FXR null mice demonstrate that FXR plays a role in bile acid homeostasis, and it therefore plays a role in lipid homeostasis by virtue of the regulation of enzymes and transporters that are involved in lipid catabolism and excretion. FXR therefore is a target for the treatment of a number of cholestatic liver diseases and non-alcoholic steatohepatitis.

Compounds of formula (I) are useful for the treatment of cholestatic liver disease. For example, the compounds of formula (I) are useful in the treatment of primary biliary cirrhosis or primary sclerosing cholangitis. The compounds of formula (I) are also useful for the treatment of gall stones. For example, the compounds of formula (I) are useful in the treatment of cholesterol gallstone disease. The compounds of formula (I) are also useful for decreasing liver lipid accumulation.

Compounds of formula (I) are also useful for the treatment of organ fibrosis. Fibrotic disorders can be characterized as acute or chronic, but share the common characteristic of excessive collagen accumulation and an associated loss of function as normal tissues are replaced or displaced by fibrotic tissues. Acute forms of fibrosis include response to trauma, infections, surgery, burns, radiation and chemotherapy. Chronic forms of fibrosis may be due to viral infection, diabetes mellitus, obesity, fatty liver, hypertension, scleroderma and other chronic conditions that induce fibrosis.

Organs that are most commonly affected by fibrosis include liver and kidney. Organ fibrosis can cause the progressive loss of organ function. Retroperitoneal fibrosis (including idiopathic retroperitoneal fibrosis) may not originate from any major organ, but can involve and adversely affect the function of organs such as the kidneys.

Accordingly, as used herein, the term fibrosis refers to all recognized fibrotic disorders, including fibrosis due to pathological conditions or diseases, fibrosis due to physical trauma ('traumatic fibrosis'), fibrosis due to radiation damage, and fibrosis due to exposure to chemotherapeutics. As used herein, the term "organ fibrosis" includes but is not limited to liver fibrosis, fibrosis of the kidneys, and fibrosis of the intestine.

"Traumatic fibrosis" includes but is not limited to fibrosis secondary to surgery (surgical scarring), accidental physical trauma, burns, and hypertrophic scarring.

In one particular embodiment, compounds of formula (I) are useful for the treatment of liver fibrosis in a subject, particularly a mammal such as a human, in need of treatment thereof. As used herein, "liver fibrosis" includes liver fibrosis due to any cause, including but not limited to virally-induced liver fibrosis such as that due to hepatitis B or C virus; exposure to alcohol (alcoholic liver disease), pharmaceutical compounds, oxidative stress, cancer radiation therapy or industrial chemicals; and diseases such as primary biliary cirrhosis, primary sclerosing colangitis, fatty liver, obesity, non-alcoholic steatohepatitis, cystic fibrosis, hemochromatosis, autoimmune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis. Other strategies for treating liver fibrosis are under development (see, e.g., Murphy et al., Expert Opin. Investig. Drugs 11:1575 (2002); Bataller and Brenner, Semin. Liver Dis. 21:437 (2001)). Thus in another embodiment, the present invention provides a method for the treatment of liver fibrosis in a subject which comprises administering a therapeutically effective amount of a compound of formula (I) in combination with another therapeutic agent useful for the treatment of symptoms associated with liver fibrosis. Examples of therapeutic agents useful for the treatment of symptoms associated with liver fibrosis include corticosteroids and cholchicine.

The response of the liver to hepatocellular damage, similar to wound healing in other tissues, includes inflammation and tissue remodeling, with associated changes in the quantity and quality of the extracellular matrix. Progressive accumulation of extracellular matrix proteins, including collagen types I and III, eventually distorts the architecture of the liver by forming fibrous scars, resulting in disrupted blood flow and an eventual deterioration in hepatic function. Hepatic stellate cells (HSC) have been identified as important mediators of the fibrotic process in the liver, and are believed to be primarily responsible for the synthesis of excess extracellular matrix seen in liver disease. Liver injury can result in quiescent HSCs converting to activated myofibroblast-like cells that proliferate, migrate, recruit inflammatory cells, and synthesize collagens and other extracellular matrix proteins. Various cytokines are reported to activate HSCs, including transforming growth factor β (TGFβ). Following liver injury, HSCs synthesize α-smooth muscle actin (α-SMA) as part of the migration response, consequently a marked accumulation of α-SMA can be seen at areas of active liver fibrogenesis. Derangement of normal the epithelial/mesenchymal interaction, characterised by cholangiocyte damage/proliferation, can also lead to extracellular matrix-producing and progressive fibrogenesis. Pinzani M. et al., Dig. Liver Dis., 36:231-242 (2004).

As is known in the art, liver fibrosis may be clinically classified into five stages (S0 to S4) of severity, usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

Compounds of formula (I) are also useful for the treatment of non-alcoholic fatty liver disease and non-alcoholic steatohepatitis in a subject, such as a mammal, particularly a human.

Compounds of formula (I) are useful for lowering triglycerides in a subject, such as a mammal, particularly a human. As used herein "lowering triglycerides" means lowering triglycerides in a subject in need thereof below the initial level of triglyercides in that subject before administration of a compound of formula (I). For example, the compounds of formula (I) may lower triglycerides by decreasing fat absorption, decreasing hepatic triglyceride production or decreasing hepatic triglyceride secretion. Compounds of formula (I) may also lower serum and hepatic triglycerides Compounds of formula (I) are also useful for the treatment of depression. For example, compounds of formula (I) may be useful for the treatment of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; demential of the Alzheimer's type, with early or late onset, with depressed mood; vascular dementia with depressed mood; mood disorders induced by alcohol, amphetamines, cocaine, hallucinogen, inhalants, opioids, phenylcyclidine, sedatives, hypnotics, anxiolytics and other substances; schizoaffective disorder of the depressed type, and adjustment disorder with depressed mood. Major depressive disorders may also result from a general medical condition including, but not limited to, myocardial infarction, diabetes mellitus, miscarriage or abortion.

Compounds of formula (I) are also useful for the treatment of diabetes mellitus in a subject, such as a mammal, particularly a human. For example, the compounds of formula (I) are useful for the treatment of type 2 diabetes. The effects of an FXR agonist, GW4064, on body weight, glucose tolerance, serum glucose, serum insulin, serum triglyceride, and liver triglyceride contents via oral administration have been observed in an high-fat diet induced insulin resistant, glucose intolerant, and obese mouse model. Male 20 to 25 g C57BL mice (Charles River, Indianapolis, Ind.) were housed at 72° F. and 50% relative humidity with a 12 h light and dark cycle and fed with standard rodent chow (Purina 5001, Harlan Teklad, Indianapolis, Ind.) or a high-fat diet (TD93075, Harlan Teklad, Indianapolis, Ind.) for seven weeks. After two weeks, mice on high-fat diet were randomized to vehicle or treatment groups. There were no significant difference in body weight, body fat mass, serum glucose and insulin, and area under the curve (AUC) for glucose in glucose tolerance test (GTT) between the vehicle group and the treatment group. Starting from the fourth week, mice were given either vehicle or GW4064 (100 mg/kg) twice a day orally. Mice on the standard rodent chow were also given vehicle as a control. At the end of the third week of compound treatment, a GTT was performed and body composition was measured using the quantitative magnetic resonance (QMR) method. At the end of the study (fourth week of compound treatment), blood samples were taken from inferior vena cava and tissue samples were collected for further analysis. Blood glucose during GTT was measured using Bayer Glucometer Elite® XL. Serum chemistry levels were measured using the Instrumentation Laboratory Ilab600™ clinical chemistry analyzer (Instrumentation Laboratory, Boston, Mass.). Liver triglyceride contents were measured using the methanolic-KOH saponification method and a triglyceride assay kit (GPO-TRINDER, Sigma Diagnostics, St. Louis, Mo.). The results indicated that GW4064 reduced the high-fat diet induced body weight gain. It is believed that the result may have been due to a decrease in fat mass. GW4064 also appeared to improve glucose tolerance, decreased serum glucose, insulin and triglyceride, and reduced liver triglyceride content. This data suggest that FXR agonists, including the compounds of the formula (I), may be used for the treatment of obesity, insulin resistance, glucose intolerance, diabetes mellitus, fatty liver disease and metabolic syndrome.

Compounds of formula (I) are also useful for the treatment of metabolic syndrome in a subject, such as a mammal, particularly a human. Metabolic syndrome is characterized by a group of metabolic risk factors in one person. They include abdominal obesity (excessive fat tissue in and around the abdomen), atherogenic dyslipidemia (high triglycerides, low high density lipoprotein (HDL) cholesterol and high low density lipoprotein (LDL) cholesterol), elevated blood pressure, insulin resistance or glucose intolerance, prothrombotic state and proinflammatory state. People with metabolic syndrome are at increased risk of coronary heart disease and atherosclerosis-related diseases (e.g., stroke and peripheral vascular disease) and type 2 diabetes mellitus. It is estimated that over 50 million people have metabolic syndrome in the United States. [http://www.americanheart.org/]. The present invention provides a method for the treatment of metabolic syndrome characterized by abdominal obesity, atherogenic dyslipidemia and insulin resistance, and may benefit other components of metabolic syndrome in a subject.

The present invention provides a method for the treatment of a condition mediated by FXR in a subject, such as a mammal, particularly a human, in need thereof. In particular, the present invention provides methods for the treatment of cardiovascular disease including artherosclerosis and hypercholesteremia. The present invention also provides the use of a compound of formula (I) for the preparation of a medicament for the treatment of a condition mediated by FXR, including cardiovascular disease.

The present invention provides a method for the treatment of cholestatic liver disease in a subject, such as a mammal, particularly a human, in need thereof. The present invention also provides the use of a compound of formula (I) for the preparation of a medicament for the treatment of cholestatic liver disease in a subject.

The present invention provides a method for the treatment of organ fibrosis in a subject, such as a mammal, particularly a human, in need thereof. The present invention also provides the use of a compound of formula (I) for the preparation of a medicament for the treatment of organ fibrosis in a subject.

The present invention provides a method for the treatment of liver fibrosis in a subject, such as a mammal, particularly a human, in need thereof. The present invention also provides the use of a compound of formula (I) for the preparation of a medicament for the treatment of liver fibrosis in a subject.

The present invention provides a method for the treatment of diabetes mellitus in a subject, such as a mammal, particularly a human, in need thereof. The present invention also provides the use of a compound of formula (I) for the preparation of a medicament for the treatment of diabetes mellitus in a subject.

The present invention provides a method for the treatment of metabolic syndrome in a subject, such as a mammal, particularly a human, in need thereof. The present invention also provides the use of a compound of formula (I) for the preparation of a medicament for the treatment of metabolic syndrome in a subject.

The present invention provides a method for the treatment of obesity in a subject, such as a mammal, particularly a human, in need thereof. The present invention also provides the use of a compound of formula (I) for the preparation of a medicament for the treatment of obesity in a subject.

The present invention also provides a method for lowering triglycerides in a subject, such as a mammal, particularly a human, in need thereof. The present invention also provides the use of a compound of formula (I) for the preparation of a medicament for lowering triglycerides in a subject.

The present invention provides a method for the treatment of depression in a subject, such as a mammal, particularly a human, in need thereof. The present invention also provides the use of a compound of formula (I) for the preparation of a medicament for the treatment of depression in a subject.

All of the methods of the present invention comprise the step of administering a therapeutically effective amount of the compound of formula (I) or a pharmaceutically acceptable salt or solvate thereof. As used herein, the term "therapeutically effective amount" refers to an amount of the compound of formula (I) which is sufficient to achieve the stated effect in the subject to which it is administered. Accordingly, a therapeutically effective amount of a compound of formula (I) used in the method for the treatment of a condition mediated by FXR in a human will be an amount sufficient for the treatment of the condition mediated by FXR in a human. A therapeutically effective amount of a compound of formula (I) for use in the method for the treatment of cholestatic liver disease in a human will be an amount sufficient for the treatment of cholestatic liver disease in a human. A therapeutically effective amount of a compound of formula (I) for use in the method for the treatment of organ (e.g., liver) fibrosis in a human will be an amount sufficient for the treatment of organ fibrosis in a human. A therapeutically effective amount of a compound of formula (I) for use in the method for the treatment of diabetes mellitus in a human will be an amount sufficient for the treatment of diabetes mellitus in a human. A therapeutically effective amount of a compound of formula (I) for use in the method for the treatment of depression in a human will be an amount sufficient for the treatment of depression in a human.

The amount of a compound of formula (I) which is required to achieve the desired therapeutic or biological effect will depend on a number of factors such as the use for which it is intended, the means of administration, the recipient and the type and severity of the condition or disease being treated, and will be ultimately at the discretion of the attendant physician or veterinarian. In general, a typical daily dose for the treatment of an FXR mediated disease or condition in a human, for instance, may be expected to lie in the range of from about 0.01 mg/kg to about 100 mg/kg for a 70 kg human. This dose may be administered as a single unit dose or as several separate unit doses or as a continuous infusion. Similar dosages would be applicable for the treatment of other diseases, conditions and therapies including diabetes mellitus and obesity in humans.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers or diluents. The carrier(s) and/or diluent(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers and/or diluents.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

A compound of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range of about 20 microns to about 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. Thus, the present invention also encompasses pharmaceutical compositions further comprising one or more therapeutic agents. In one embodiment, the pharmaceutical compositions further comprise one or more lipid-altering agents. Examples of lipid-altering agents include but are not limited to liver X receptor (LXR) agonists described in PCT Publication No. WO02/24632 to GlaxoSmithKline).

Examples of other therapeutic agents include, but are not limited to, 3-Hydroxy-3-Methyl-Glutaryl-CoA reductase inhibitors such as statins (atorvastatin, fluvastatin, pravastatin, lovastatin, cerivastatin, and nisvastatin); squalene epoxidase inhibitors, squalene synthetase inhibitors, bile acid transport inhibitors (BATi), human peroxisome proliferator activated receptor (PPAR) gamma agonists such as rosiglitazone, troglitazone, and pioglitazone and thiazolidinediones; PPAR α agonists such as clofibrate, fenofibrate and gemfibronzil; PPAR dual α/γ agonists; cyclooxygenase-2 (COX-2) inhibitors such as rofecoxib and celecoxib; thrombin inhibitors; acyl-coenzyme A; cholesterol acyltransferase (ACAT) inhibitors including selective ACAT inhibitors; microsomal triglyceride transfer protein (MTP) inhibitors; probucol, niacin; cholesterol absorption inhibitors; bile acid sequestrants; LDL receptor inducers; platelet aggregation inhibitors such as glycoprotein IIb/IIIa fibrinogen receptor antagonists and aspirin; vitamin B6 and pharmaceutically acceptable salts thereof; vitamin B12; folic acid or a pharmaceutically acceptable salt or ester thereof, antioxidant vitamins such as C and E and beta carotene; beta blockers; angiotensin II antagonists such as losartan; antiotensin converting enzyme inhibitors such as enalapril and captopril; calcium channel blockers such as nifedipine and diltiazam; endothelian antagonists; agents other than LXR ligands that enhance ATP-Binding Cassette Transporter-A1 gene expression; and bisphosphonate compounds such as alendronate sodium.

The methods and uses employing these combinations may comprise the administration of the compound of formula (I) and another therapeutic agent either sequentially in any order or simultaneously in separate or combined pharmaceutical compositions. When combined in the same composition it will be appreciated that the compounds must be stable and compatible with each other and the other components of the composition and may be formulated for administration. When formulated separately they may be provided in any convenient formulation, in such a manner as are known for such compounds in the art.

When a compound of formula (I) is used in combination with another therapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Compounds of the invention can be made according to any suitable method of organic chemistry. According to one method, a compound of formula (I) may be prepared using the process depicted in Scheme 1, below.

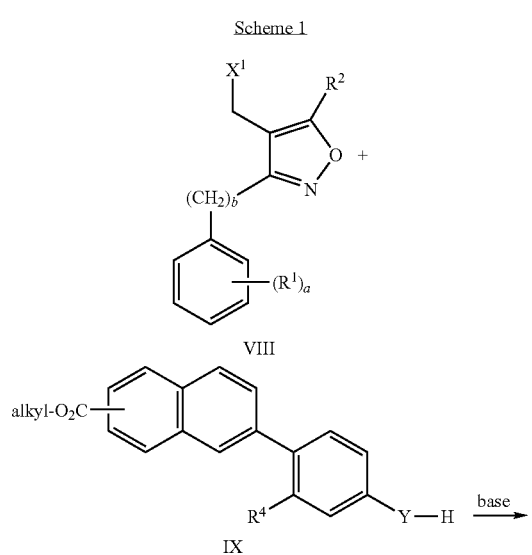

Scheme 1

-continued

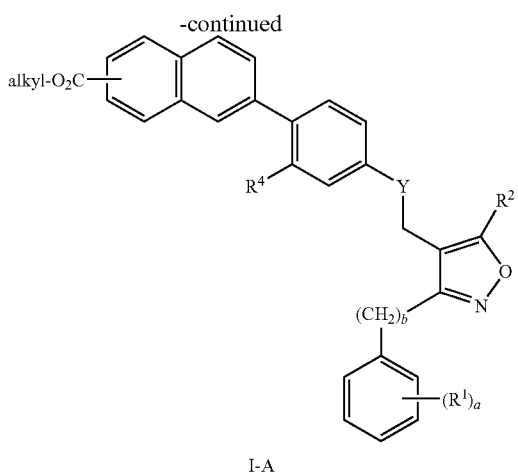

I-A wherein:
X[1] is chloro, iodo, bromo, triflate, tosylate, nosylate, besylate or mesylate, (preferably chloro); and
all other variables are as defined above.

In general, the process of Scheme 1 comprises the steps of:
a) reacting a compound of formula (VIII) with a compound of formula (IX) to prepare a compound of formula (I-A);
b) optionally converting the compound of formula (I-A) into a different compound of formula (I).

More particularly, the compound of formula (I-A) may be prepared by reacting the compound of formula (XI) with a compound of formula (VIII) in the presence of a suitable base such as cesium carbonate or potassium carbonate, in a polar aprotic solvent such as N,N-dimethylformamide at ambient or elevated temperature.

The compound of formula (VIII) may be prepared by reacting a compound of formula (VIII-B) with the appropriate reagent to produce a compound with the desired leaving group (X[1]).

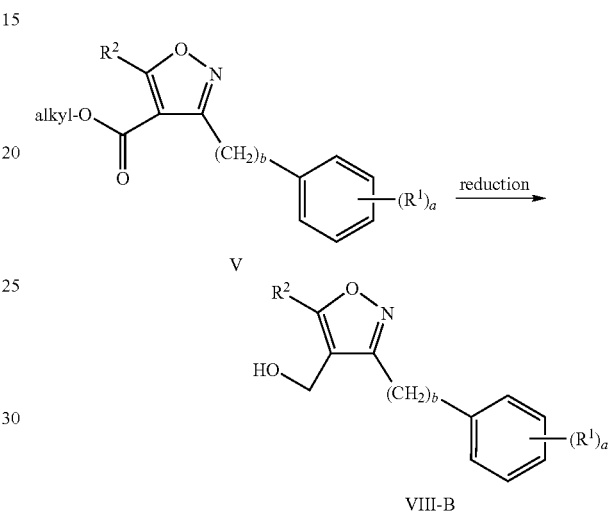

wherein all variables are as defined above.

When X[1] is halo, the reaction is performed by halogenating the compound of formula (VIII-B). Any suitable halogenating reagent conventional in the art may be employed in the reaction. Examples of suitable halogenating reagents include, but are not limited to, thionyl chloride or triphenylphosphine dichloride. The reaction is typically carried out in a non-polar solvent such as dichloromethane or 1,2-dichloroethane at ambient temperature.

Wherein X[1] is triflate, tosylate or meslyate, the reaction process may be carried out according to the methods described by Vedejs, E. et al.; *J. Org. Chem.* 42: 3109-3113 (1977), Handy, S. T.; et al.: *J. Org. Chem.* 69, 2362-2366 (2004), or Copp, T.; et al. *Journal of the Chemistry Society* 2021-2025 (1955) respectively.

The compound of formula (VIII-B) may be prepared by reducing a compound of formula (V).

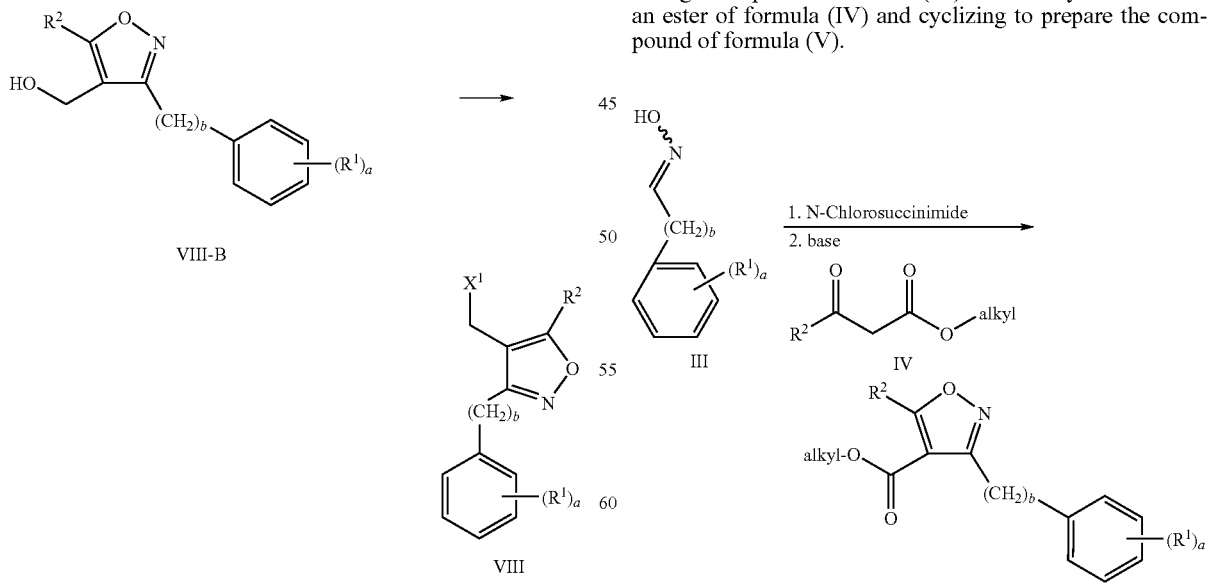

wherein all variables are as defined above.

A compound of formula (V) may be treated with a reducing agent such as diisobutylaluminum hydride, in a suitable solvent such as tetrahydrofuran.

The compound of formula (V) may be prepared by chlorinating a compound of formula (III) followed by reaction with an ester of formula (IV) and cyclizing to prepare the compound of formula (V).

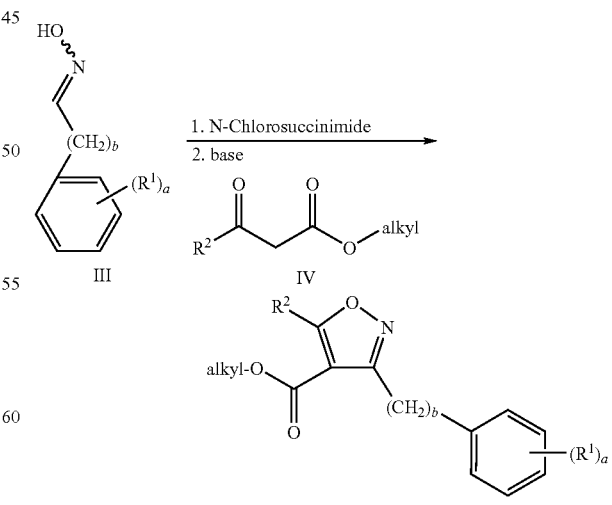

wherein all variables are as defined above.

The process is conveniently carried out according to the method described by Doyle, H. P., et. al., *Journal of the Chemical Society* Part V:5838 (1963). Esters of formula (IV) are commercially available or can be prepared using conventional techniques.

The compound of formula (III) may be prepared by condensing a compound of formula (II) with hydroxylamine.

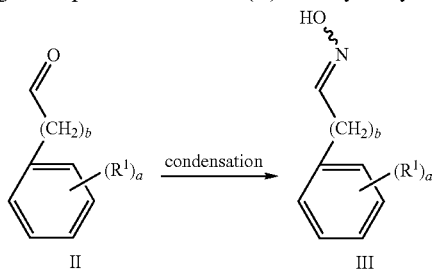

wherein all variables are as defined above.

Alternatively, a compound of formula (V) may be prepared by reacting a compound of formula (VII) with tin chloride in the presence of a compound of formula (IV) followed by treatment with hydroxylamine to yield a compound of formula (V) (Singh, B.; Lesher, G. Y.; *Synthesis*, 829-830 (1978)). The compound of formula (VII) may be obtained commercially or by procedures in the literature (Guo, H.; Zhang, Y.; *Synth. Commun.*, 30, 1879-1886 (2000)). The compound of formula (V) may then be reduced with diisobutylaluminum hydride to prepare a compound of formula (VIII-B) in the manner described above.

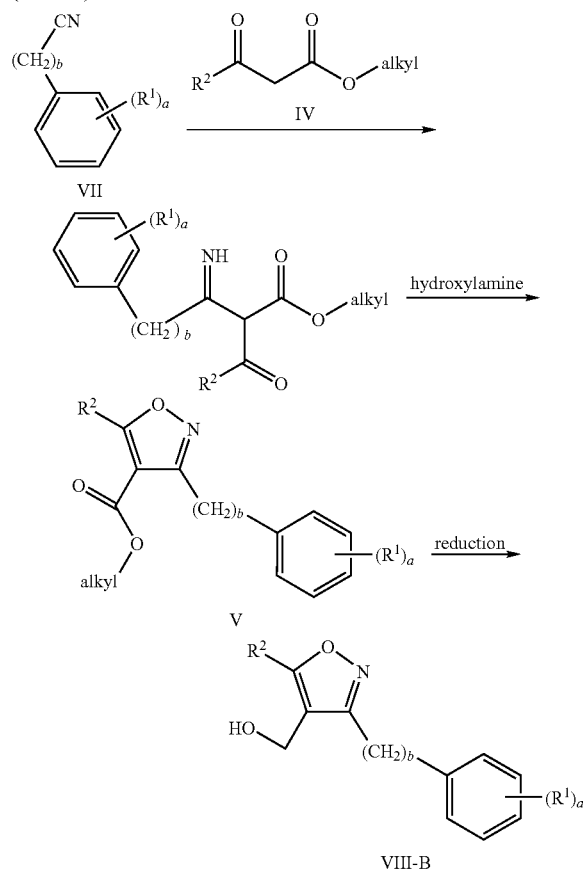

wherein all variables are as defined above.

A compound of formula (IX) may be prepared by a two-step process comprising
a) reacting the phenol of formula (X) with a reagent suitable for installation of the leaving group to prepare a compound of formula (XI) and
b) coupling the compound of formula (XI) with a compound of formula (XII) to prepare the compound of formula (IX).

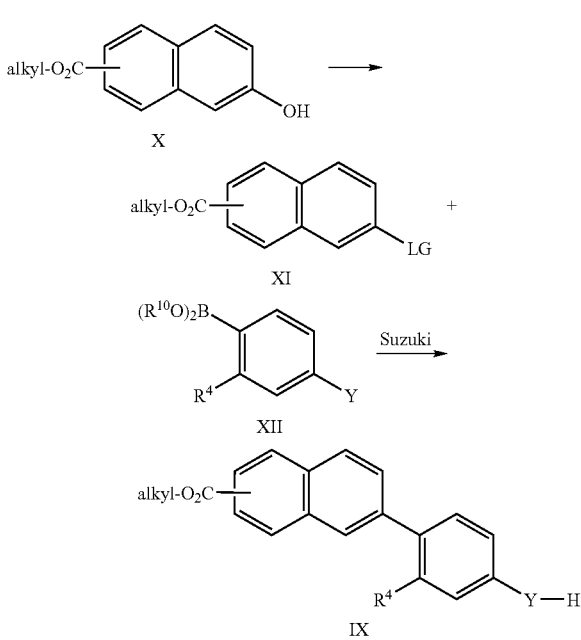

wherein LG is chloro, bromo, iodo, or triflate;
$R^{10}$ is H or alkyl; and
all other variables are as defined above.

Compounds of formula (X) are commercially available or can be prepared from the corresponding acid using techniques well-known in the art.

Compounds of formula (XI) are commercially available or may be prepared by reacting the compound of formula (X) with triflic anhydride using techniques conventional in the art. For example, a compound of formula (XI) may be prepared by reacting the compound of formula (X) with triflic anhydride in a solution of dichloromethane with an appropriate base such as pyridine. Alternatively, a compound of formula (XI) may be prepared by reacting the compound of formula (X) in a suspension of toluene with an aqueous solution of tribasic potassium phosphate and then reacting with triflic anhydride.

The compounds of formula (XI) are reacted with the boronic acid or ester of formula (XII) to prepare the compound of formula (IX). This reaction may be carried out using conventional Suzuki coupling techniques. For example, the compound of formula (IX) may be prepared by coupling a compound of formula (XII) with a compound of formula (XI) in the presence of a suitable palladium complex such as tetrakis(triphenylphosphine)palladium(0) and a base such as sodium carbonate in a mixture of water and ethereal solvent like 1,2-dimethoxyethane at an elevated temperature.

In another embodiment, compounds of formula (I) may be prepared according to Scheme 2.

Scheme 2

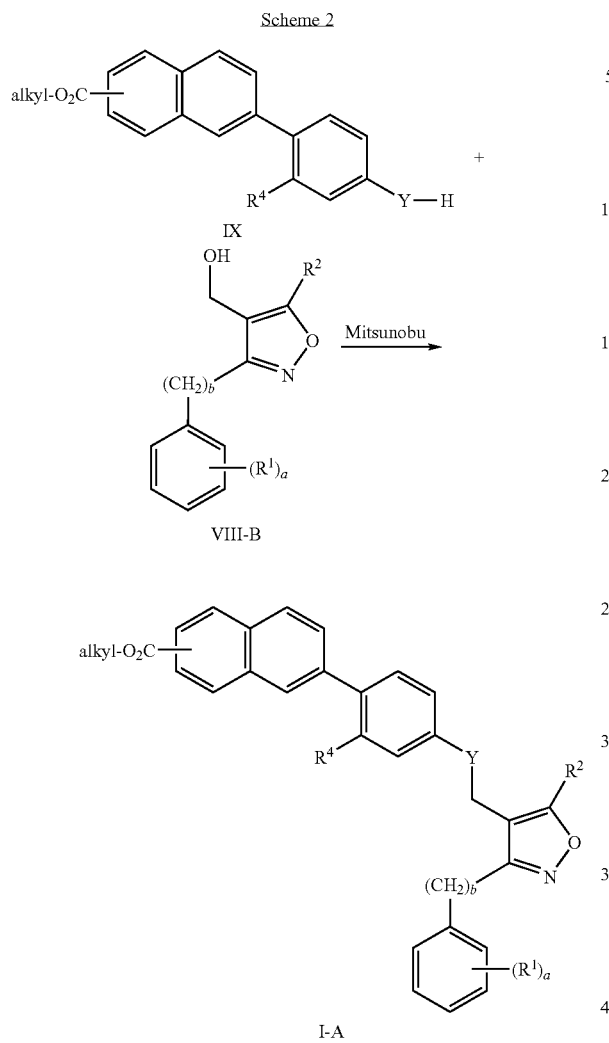

wherein all variables are as defined above.

In general, the process of Scheme 2 comprises the steps of:
a) reacting a compound of formula (VIII-B) with a compound of formula (IX) to prepare a compound of formula (I-A);
b) optionally converting the compound of formula (I-A) into a different compound of formula (I).

More specifically, the compound of formula (I-A) is prepared by reacting the compound of formula (IX) with a compound of formula (VIII-B). Typically, the reaction of the compound of formula (IX) with the compound of formula (VIII-B) is carried out under Mitsunobu conditions. For example, a compound of formula (I-A) can be prepared by the reaction of a compound of formula (IX) with an alcohol of formula (VIII-B) in a solution of dichloromethane or toluene with triphenyl phosphine and diisopropyl azodicarboxylate. To prepare compounds of formula (IX) wherein Y is $NR^8$ it may be desirable to first form the trifluoroacetamide derivative of the compound of formula (IX) before performing the Mitsunobu reaction. The product of the Mitsunobu reaction may then be converted by one skilled in the art to produce desired substitution ($R^8$) on the amine. The compound of formula (VIII-B) may be prepared by methods similar those described above.

As will be apparent to those skilled in the art, a compound of formula (I) may be converted to a different compound of formula (I) using techniques well known in the art. For example, compound of formula (I-A) made be converted to the corresponding acid (i.e. a compound of formula (I-B)) by saponification with a suitable base such as sodium hydroxide in a solution of water and tetrahydrofuran and optionally an alcoholic co-solvent that corresponds to the ester to be saponified.

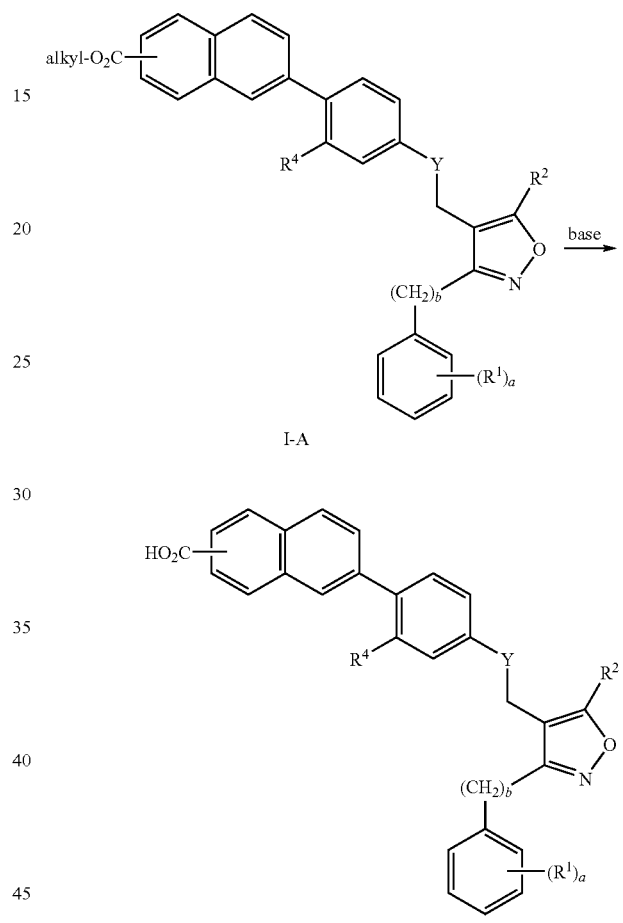

In one embodiment, the process of the present invention includes the further step of converting the compound of formula (I-B) into a pharmaceutically acceptable salt or solvate thereof.

In another embodiment, the process comprises the further step of optionally converting the compound of formula (I-B) or a pharmaceutically acceptable salt or solvate thereof into a different compound of formula (I) or a pharmaceutically acceptable salt or solvate thereof.

For example, a compound of formula (I-B) may be reacted with an amine to prepare the corresponding amide (i.e. a compound of formula (I-C)). This reaction may be carried out using conventional techniques. For example, a compound of formula (I-B) may be reacted with di-tert-butyl dicarbonate in acetonitrile with a base such as pyridine then ammonium hydrogen carbonate to produce a compound of formula (I-C). (C. D. Haffner, et al., US2004/0171848).

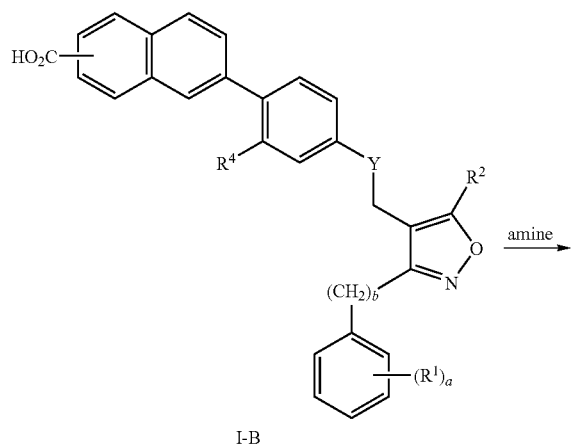

I-B

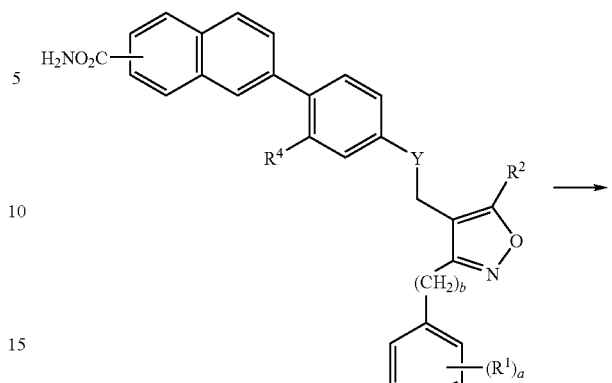

I-C

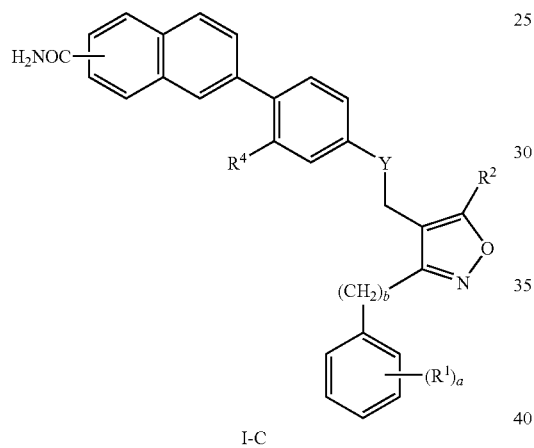

I-C

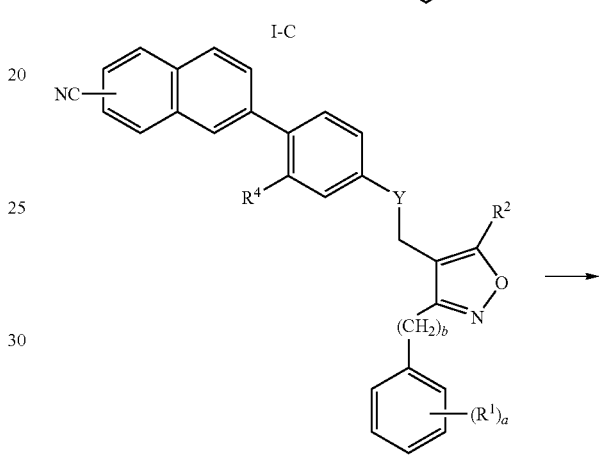

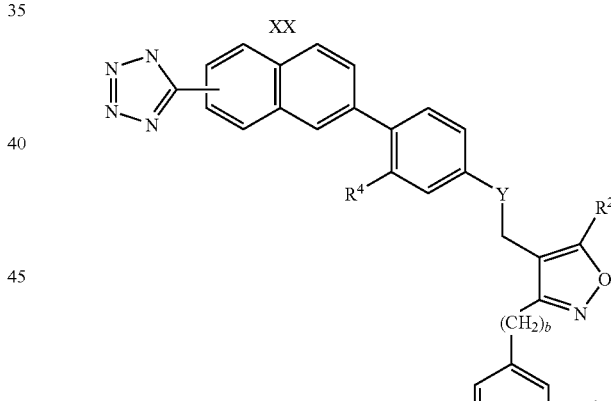

I-D

As another example of converting a compound of formula (I) to another compound of formula (I). A compound of formula (I-C) may be dehydrated to prepare a corresponding nitrile (i.e. a compound of formula (XX)). This reaction may be carried out using conventional amide dehydration techniques. For example, a compound of formula (I-C) may be dehydrated with phosphorous oxychloride in a solution of methylene chloride and a suitable base such as triethylamine to prepare a compound of formula (XX). (P. G. H. Uiterweerd, et al., *Tetrahedron: Asymmetry*, 14: 3479-3486 (2003)). A compound of formula (XX) may be condensed with sodium azide to prepare a corresponding tetrazole (i.e. a compound of formula (I-D)). This reaction may be carried out using conventional techniques. For example, a compound of formula (I-D) may be prepared by reacting a compound of formula (XX) with sodium azide in the presence of ammonium chloride in a polar aprotic solvent such as N,N-dimethylformamide at an elevated temperature. (E. Meyer, et al., *Synthesis* 29: 899-905 (2003)).

Based upon these examples and the disclosure contained herein one skilled in the art can readily convert compounds of formula (I) into other compounds of formula (I), or salts, solvates or physiologically functional derivatives thereof. For example, a compound of formula (XX) may be converted to a compound in which CN is replaced with an acid-equivalent group according to the methods described in J. W. Ellingboe, et al., *J. Med. Chem.*; 36 2485-2493 (1993) and H. N. Weller, et al., *Heterocycles* 36 1027-1038 (1993).

The following examples are intended for illustration only and are not intended to limit the scope of the invention in any way, the present invention being defined by the claims.

In the examples, the following terms have the designated meaning:

| | |
|---|---|
| g = | gram; |
| mg = | milligram; |
| mol = | mole; |
| mmol = | millimole; |
| M = | molar; |
| mM = | millimolar; |
| μM = | micromolar; |
| N = | normal; |
| L = | liter; |
| mL = | milliliter; |
| μL = | microliter; |
| cm = | centimeter; |
| h = | hour; |
| min = | minute; |
| rt = | room temperature; |
| aq = | aqueous; |
| Me = | methyl; |
| Et = | ethyl; |
| EtOAc = | ethyl acetate; |
| hex = | hexane; |
| THF = | tetrahydrofuran; |
| $N_2$ = | nitrogen; |
| $CH_2Cl_2$ = | dichloromethane; |
| $H_2O$ = | water; |
| $SiO_2$ = | silicon dioxide; |
| $P_2O_5$ = | phosphorus pentoxide; |
| NaF = | sodium fluoride; |
| NaOH = | sodium hydroxide; |
| $MgSO_4$ = | magnesium sulfate; |
| $Na_2SO_4$ = | sodium sulfate; |
| DMF = | N,N-dimethylformamide; |
| DMSO = | dimethylsulfoxide; |
| $P_2O_5$ = | phosphorus pentoxide; |
| $K_2CO_3$ = | potassium carbonate; |
| $PO_4$ = | phosphate; |
| $Na_2CO_3$ = | sodium carbonate; |
| $NaHCO_3$ = | sodium hydrogen carbonate; |
| HCl = | hydrogen chloride; |
| ≈ = | a mixture of geometric isomers; |
| NMR = | nuclear magnetic resonance; |
| H = | Hydrogen; |
| Hz = | Hertz; |
| OD = | optical density; |
| HRMS = | High Resolution Mass Spectrometry; |
| APCI-LCMS = | Atmospheric Pressure Chemical Ionization-Liquid Chromatography Mass Spectrometry; |
| ESI-LCMS = | Electrospray Ionization-Liquid Chromatography Mass Spectrometry. |

EXAMPLE 1

6-[4-({[3-(2,6-Dichlorophenyl)-5-(1-methylethyl)-4-isoxazolyl]methyl}oxy)phenyl]-1-naphthoic Acid Sodium Salt

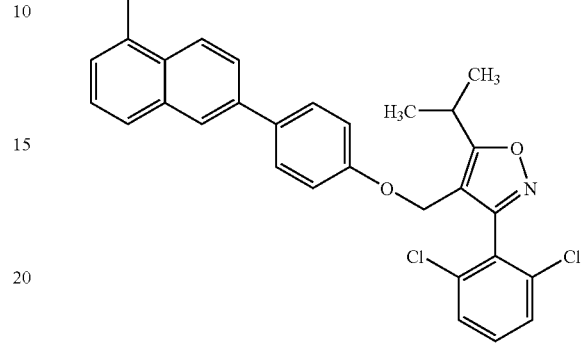

1a) Methyl 6-hydroxy-1-naphthoate

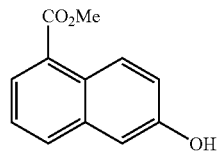

Methanesulfonic acid (18 mL, 0.28 mol) was added to a stirred solution of 6-hydroxy-1-naphthoic acid (262 g, 1.39 mol) in methanol (1 L) under $N_2$ and the reaction mixture was heated at reflux for 18 h. The reaction mixture was cooled to room temperature and concentrated to give a purple solid. The solid was dissolved in ethyl acetate (1 L), washed with water (3×300 mL), saturated sodium bicarbonate solution (2×300 mL), water (500 mL), brine (300 mL) and then dried over anhydrous sodium sulfate. The resulting solution was filtered and concentrated to give 271 g of the product as a pink solid. $^1$H NMR (400 MHz, $d_6$-DMSO): δ 9.94 (s, 1H), 8.58 (m, 1H), 7.93 (d, J=8 Hz, 1H), 7.86 (d, J=7.0 Hz, 1H), 7.44 (t, J=8 Hz, 1H), 7.22-7.19 (m, 2H), 3.88 (s, 3H). ESI-LCMS m/z 203 $(M+H)^+$.

1b) Methyl 6-{[(trifluoromethyl)sulfonyl]oxy}-1-naphthoate

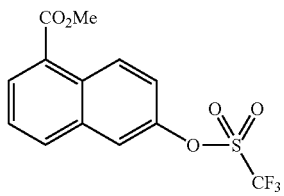

An ice-cold mechanically stirred suspension of methyl 6-hydroxy-1-naphthoate (138 g, 0.68 mol) in toluene (1.3 L) was treated with a solution of tribasic potassium phosphate (414 g, 2 mol) in water (1.6 L). The resulting mixture was treated dropwise with triflic anhydride (142 mL, 0.84 mol) at a rate to maintain the reaction temperature at 25° C. After 1 hour triflic anhydride (56 mL, 0.33 mol) was added and stirring was continued. After 45 minutes another addition of triflic anhydride (30 mL, 0.18 mol) was made. After 20 min the toluene layer was separated and washed with water. The toluene layer was stirred with a fresh solution of tribasic potassium phosphate (106 g, 0.5 mol) in water (325 mL). Triflic anhydride (40 mL, 0.24 mol) was added dropwise. After approximately 20 minutes the layers were separated. The toluene layer was washed with water (2×400 mL) and concentrated to give 232 g of a brick-red solid (assume theoretical yield). $^1$H NMR (DMSO-$d_6$): δ 8.92 (d, J=10 Hz, 1H), 8.33 (d, J=8 Hz, 1H), 8.27 (m, 1H), 8.24 (d, J=7 Hz, 1H), 7.77-7.72 (m, 2H), 3.93 (s, 3H). ESI-LCMS m/z 335 (M+H)$^+$.

Alternate 1b) Methyl 6-{[(trifluoromethyl)sulfonyl]oxy}-1-naphthoate

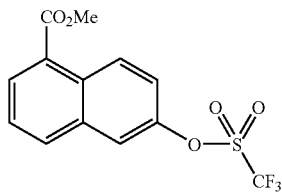

An ice-cold mechanically stirred suspension of methyl 6-hydroxy-1-naphthoate in toluene is treated with a solution of tribasic potassium phosphate in water. The resulting mixture is treated dropwise with triflic anhydride at a rate to maintain the reaction temperature at 25° C. After 30 min the toluene layer is separated, washed with water and concentrated the product is yielded.

1c) Methyl 6-(4-hydroxyphenyl)-1-naphthoate

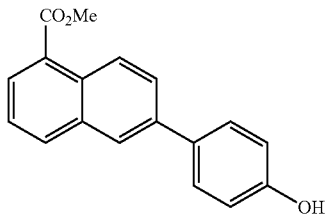

A solution of methyl 6-{[(trifluoromethyl)sulfonyl]oxy}-1-naphthoate (271 g, 0.81 mol) (from multiple batches), tetrakis(triphenylphospine)palladium (0) (37.4 g, 0.032 mol), 2 M sodium carbonate solution (1.3 L) and 4-hydroxyphenyl boronic acid (134 g, 0.97 mol) in ethylene glycol dimethyl ether (1.5 L) was heated at 80° C. for 1.5 h. The reaction mixture was cooled to room temperature and diluted with ethyl acetate (2 L) and water (2 L). The ethyl acetate layer was dried over anhydrous sodium sulfate, filtered and concentrated to a dark semisolid residue. The crude material was purified by crystallization from dichloromethane-heptane to give 199 g of the product as a tan solid.

$^1$H NMR (DMSO-$d_6$): δ 9.64 (s, 1H), 8.76 (d, J=9 Hz, 1H), 8.21 (m, 2H), 8.07 (d, J=7 Hz, 1H), 7.93 (m, 1H), 7.66 (d, J=9 Hz, 2H), 7.58 (t, J=8 Hz, 1H), 6.89 (d, J=9 Hz, 2H), 3.93 (s, 3H).

1d) 4-(Chloromethyl)-3-(2,6-dichlorophenyl)-5-(1-methylethyl)isoxazole

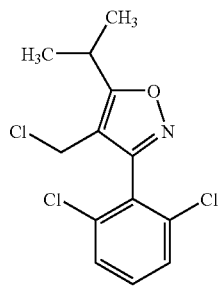

Thionyl chloride (87 mL, 1.20 mol) was added dropwise to a stirred solution of benzotriazole (143 g, 1.20 mol) in dichloromethane (400 mL) at room temperature. The resulting solution was added dropwise during 30 min to a stirred solution of [3-(2,6-dichlorophenyl)-5-(1-methylethyl)-4-isoxazolyl]methanol (263 g, 0.92 mol) in dichloromethane (700 mL). A very mild exothermic reaction occurred with precipitation of benzotriazole hydrochloride. The mixture was filtered to remove the benzotriazole hydrochloride. The filtrate was washed with water (2×800 mL), 1N sodium hydroxide (800 mL) and then dried over anhydrous sodium sulfate. The resulting solution was filtered and concentrated to give 288 g of the product as a pale yellow oil. $^1$H NMR (DMSO-$d_6$): δ 7.66 (m, 2H), 7.61-7.57 (m, 1H), 4.47 (s, 2H), 3.45 (septet, J=7 Hz, 1H), 1.31 (d, J=7 Hz, 6H). ESI-LCMS m/z 279 (M+H)$^+$.

1e) Methyl 6-[4-({[3-(2,6-dichlorophenyl)-5-(1-methylethyl)-4-isoxazolyl]methyl}oxy)phenyl]-1-naphthalenecarboxylate

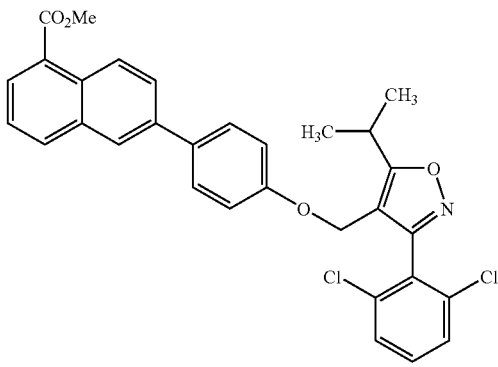

Cesium carbonate (352 g, 1.08 mol) was added to a mechanically stirred solution of methyl 6-(4-hydroxyphenyl)-1-naphthoate (199 g, 0.72 mol) in dimethylformamide (1 L) under N2. The resulting suspension was heated to 65° C. for 30 min followed by addition of 4-(chloromethyl)-3-(2,6-dichlorophenyl)-5-(1-methylethyl)isoxazole (280 g, 0.92 mol) in dimethylformamide (500 mL). The mixture was heated at 65° C. for 18 h, cooled to room temperature and partitioned between ethyl acetate (1 L) and water (1 L). The ethyl acetate layer was backwashed with water (2×1 L) and concentrated to a thick black syrup. This syrup was triturated with hexane (500 mL) and ethyl acetate (300 mL) for 2 h. Filtration gave 190 g of the product as beige crystals. $^1$H NMR (DMSO-$d_6$): δ 8.77 (d, J=9 Hz, 1H), 8.23-8.20 (m, 2H), 8.09 (d, J=7 Hz, 1H), 7.92 (dd, J=2, 9 Hz, 1H), 7.69 (d, J=9 Hz, 2H), 7.63-7.51 (m, 4H), 6.91 (d, J=9 Hz, 2H), 4.86 (s, 2H), 3.92 (s, 3H), 3.45 (septet, J=7 Hz, 1H), 1.33 (d, J=7 Hz, 6H). ESI-LCMS m/z 546 (M+H)+.

1f) 6-[4-({[3-(2,6-Dichlorophenyl)-5-(1-methylethyl)-4-isoxazolyl]methyl}oxy)phenyl]-1-naphthalenecarboxylic acid

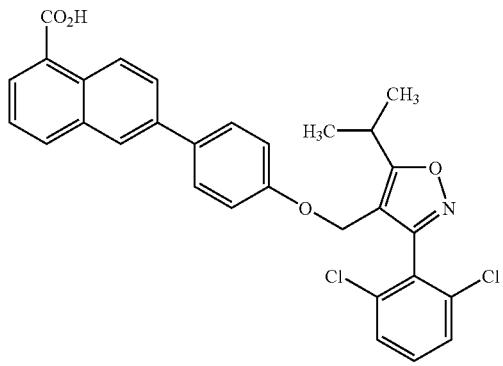

Methanol (380 mL) and 5 N sodium hydroxide solution (190 mL) were added to a stirred solution of methyl 6-[4-({[3-(2,6-dichlorophenyl)-5-(1-methylethyl)-4-isoxazolyl]methyl}oxy)phenyl]-1-naphthalenecarboxylate (190 g, 0.35 mol) in tetrahydrofuran (1 L). The resulting solution was heated to reflux for 1.5 h. The mixture was cooled to room temperature and concentrated to remove methanol and tetrahydrofuran. The residue was diluted with water (500 mL), acidified with 6 N HCl and the supernatant was decanted from the taffy-like solid. The solid was crystallized from ethyl acetate (1 L) to give 170 g of the product as off-white crystals. $^1$H NMR (DMSO-$d_6$): δ 9.02 (d, J=9 Hz, 1H), 8.01 (s, 1H), 7.80 (d, J=8 Hz, 1H), 7.73 (d, J=7 Hz, 1H), 7.68-7.61 (m, 5H), 7.53 (dd, J=7, 9 Hz, H), 7.38 (t, J=8, 15 Hz, 1H), 6.88 (d, J=9 Hz, 2H), 4.85 (s, 2H), 3.46 (septet, J=7 Hz, 1H), 1.32 (d, J=7 Hz, 6H). ESI-LCMS m/z 532 (M+H)+.

1g) 6-[4-({[3-(2,6-Dichlorophenyl)-5-(1-methylethyl)-4-isoxazolyl]methyl}oxy)phenyl]-1-naphthoic acid sodium salt

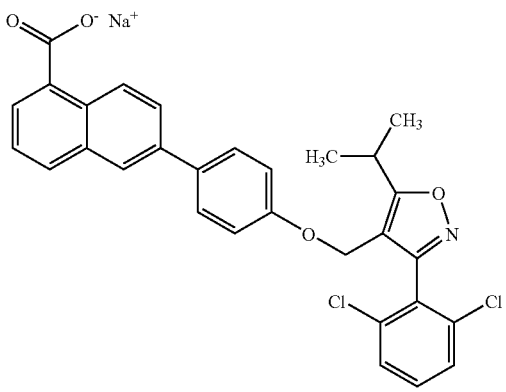

A mechanically stirred suspension of 6-[4-({[3-(2,6-dichlorophenyl)-5-(1-methylethyl)-4-isoxazolyl]methyl}oxy)phenyl]-1-naphthalenecarboxylic acid (166 g, 0.31 mol) in methanol (500 mL) was treated with 1N sodium hydroxide (327 mL). The resulting solution was stirred at room temperature. The mixture was stirred 1 h and the resulting solid was collected by filtration, washed with acetone, hexane and then dried to give 151 g of the product as a white solid. $^1$H NMR (DMSO-$d_6$): δ 9.04 (d, J=9 Hz, 1H), 8.00 (s, 1H), 7.78 (d, J=8 Hz, 1H), 7.72 (d, J=7 Hz, 1H), 7.66-7.61 (m, 5H), 7.53 (dd, J=7, 9 Hz, 1H), 7.37 (t, J=8 Hz, 1H), 6.88 (d, J=9 Hz, 2H), 4.85 (s, 2H), 3.46 (septet, J=7 Hz, 1H), 1.32 (d, J=7 Hz, 6H). ESI-LCMS m/z 532 (M+H)+.

Elemental Analysis calculated for $C_{30}H_{22}Cl_2NNaO_4 \cdot 0.75 H_2O$: C, 63.45; H, 4.17; N, 2.47; Cl, 12.49. Found: C, 63.46; H, 4.02; N, 2.50; Cl, 12.32.

EXAMPLE 2

6-[2-Chloro-4-({[3-(2,6-dichlorophenyl)-5-(1-methylethyl)-4-isoxazolyl]methyl}oxy)phenyl]-1-naphthalenecarboxylic acid

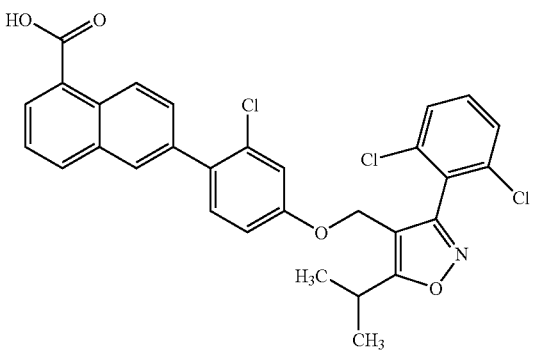

2a) Methyl 6-(2-chloro-4-hydroxyphenyl)-1-naphthalenecarboxylate

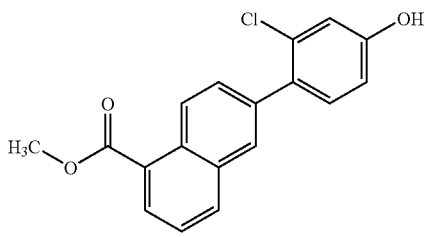

A solution of methyl 6-{[(trifluoromethyl)sulfonyl]oxy}-1-naphthoate (0.97 g, 2.91 mmol), tetrakis(triphenylphosphine) palladium (0) (0.13 g, 0.116 mmol), 2 M $Na_2CO_3$ (13.6 mL) and 2-chloro-4-[((1,1-dimethylethyl)dimethylsilyl)oxy] phenylboronic acid (1 g, 3.49 mmol) in ethylene glycol dimethyl ether (15.5 mL) was heated at 80° C. for 40 minutes. The reaction mixture was cooled to room temperature, diluted with water and EtOAc, and transferred to a separatory funnel. The organic phase was separated, washed with brine, dried over $MgSO_4$, filtered, and the filtrate was concentrated to give the crude product as an oil. The crude material was purified by flash chromatography over $SiO_2$ with a Hex:EtOAc (0 to 20% EtOAc) gradient to afford 0.74 g (82%) of the title compound as a white solid. $^1$H NMR (400 MHz, DMSO-$d_6$): δ 10.06 (s, 1 H), 8.75 (d, J=9 Hz, 1 H), 8.22 (d, J=8 Hz, 1 H), 8.13 (d, J=7

Hz, 1 H), 8.01 (s, 1 H), 7.68 (m, 1H), 7.61 (t, J=8 Hz, 1 H), 7.34 (d, J=9 Hz, 1 H), 6.96 (m, 1 H), 6.86 (m, 1 H), 3.93 (s, 3 H).

2b) Methyl 6-[2-chloro-4-({[3-(2,6-dichlorophenyl)-5-(1-methylethyl)-4-isoxazolyl]methyl}oxy)phenyl]-1-naphthalenecarboxylate

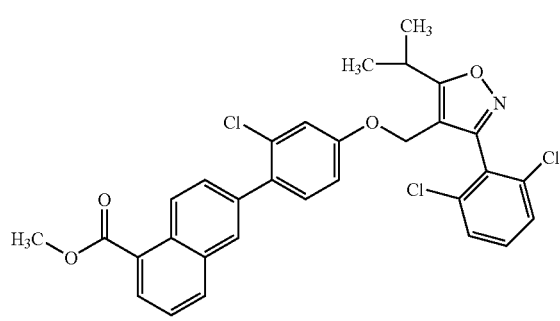

A mixture of methyl 6-(2-chloro-4-hydroxyphenyl)-1-naphthalenecarboxylate (0.25 g, 0.799 mmol), polymer-bound triphenylphosphine (0.27 g, 0.799 mmol), [3-(2,6-dichlorophenyl)-5-(1-methylethyl)-4-isoxazolyl]methanol (0.23 g, 0.799 mmol) and 10 mL of dichloromethane was cooled to 0° C. Diisopropyl azodicarboxylate (0.16 mL, 0.799 mmol) was slowly added to the reaction mixture. The reaction mixture was stirred for 10 minutes at the above temperature and then warmed to room temperature and stirred for 18 h. The reaction mixture was filtered and the filtrate was concentrated to give oil.

The crude material was partially purified by flash chromatography over silica gel using 20% EtOAc in hexane to afford 0.36 g of the title compound. $^1$H NMR (DMSO-d$_6$): δ 8.75 (d, J=9 Hz, 1H), 8.22 (d, J=8 Hz, 1H), 8.14 (d, J=7 Hz, 1H), 8.0 (s, 1H), 7.53-7.67 (m, 5H), 7.36 (d, J=8.6 Hz, 1H), 7.03-7.04 (m, 1H), 6.84-6.87 (m, 1H), 4.92 (s, 2H), 3.93 (s, 3H), 3.46 (m, 1H), 1.34 (m, 6H).

2c) 6-[2-Chloro-4-({[3-(2,6-dichlorophenyl)-5-(1-methylethyl)-4-isoxazolyl]methyl}oxy)phenyl]-1-naphthalenecarboxylic acid

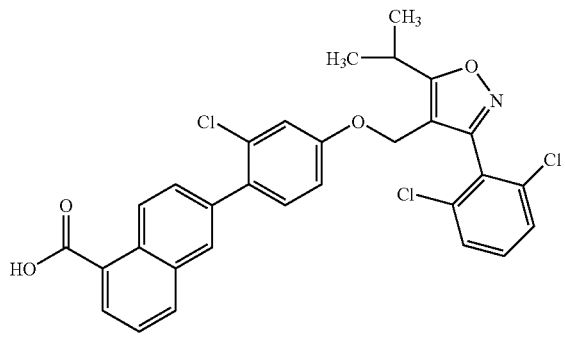

A solution of methyl 6-[2-chloro-4-({[3-(2,6-dichlorophenyl)-5-(1-methylethyl)-4-isoxazolyl]methyl}oxy)phenyl]-1-naphthalenecarboxylate (0.36 g, 0.62 mmol), 6.5 mL of THF, 3.5 mL of methanol and 1.3 mL of 1 N NaOH was stirred for 18 h at rt. The reaction mixture was heated to 65° C. for 2 hours. The solution was allowed to cool to room temperature and the pH was adjusted with 1N HCl. The solution was concentrated and the residue was extracted with ethyl acetate. The organic layer was dried with MgSO$_4$, filtered, and the filtrate was concentrated to give the crude product as oil. The crude material was purified by flash chromatography (silica gel, gradient hexane to hexanes/ethyl acetate, 1:1) to afford the title compound as a white foam (0.15 g, 67%). $^1$H NMR (DMSO-d$_6$): δ 13.13 (s, 1H), 8.87 (d, J=9 Hz, 1H), 8.19-8.14 (m, 2H), 7.97 (m, 1H), 7.64-7.53 (m, 5H), 7.36 (d, J=9 Hz, 1H), 7.04 (m, 1H), 6.86-6.84 (m, 1H), 4.92 (s, 2H), 3.48 (septet, J=7 Hz, 1H), 1.33 (d, J=7 Hz, 6 H). HRMS C$_{30}$H$_{22}$Cl$_3$NO$_4$ m/z 566.0693 (M+H)$^+_{Cal}$; 566.0687 (M+H)$^+_{Obs}$.

EXAMPLE 3

6-[4-({[5-cyclobutyl-3-(2,6-dichlorophenyl)-4-isoxazolyl]methyl}oxy)phenyl]-1-naphthalenecarboxylic acid

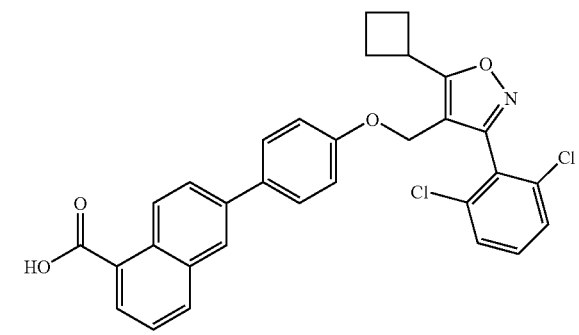

3a) Ethyl 5-cyclobutyl-3-(2,6-dichlorophenyl)-4-isoxazolecarboxylate

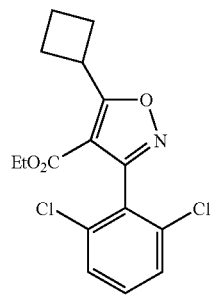

To a solution of 2,6-dichlorobenzaldehyde oxime (2.2 g, 11.6 mmol) in N,N,-dimethylformamide (7 mL) cooled in a water bath was added solid N-chlorosuccinimide (1.5 g, 11.6 mmol). The solution was stirred with the flask in the water bath for approximately 20 minutes and then with the flask out of the bath for approximately 1 hour. The solution was poured into water and then extracted twice with ether. The combined organic phases were dried over magnesium sulfate and concentrated. To a separate solution of ethyl 3-cyclobutyl-3-oxopropanoate (2.4 g, 13.9 mmol) in tetrahydrofuran (3 mL) at 0° C. was added a 3.16 M solution of sodium ethoxide in ethanol (4.4 mL, 13.9 mmol) quickly. The solution was stirred for a few minutes. To that solution was added the isolated imidoyl chloride in tetrahydrofuran (5 mL) dropwise. The solution was stirred at 0° C. for approximately 1 h and then allowed to stir at ambient temperature overnight. The solution was poured into water and extracted with ethyl acetate. The combined organic phases were dried over magnesium sulfate, concentrated and purified by chromatography (silica gel, 0-5% ethyl acetate in hexanes gradient elution) to afford a white solid (1.5 g, 38%). $^1$H-NMR (DMSO-d$_6$) δ 7.63-7.53 (m, 3H), 4.25 (quintet, J=9 Hz, 1H), 4.02 (q, J=7 Hz, 2H), 2.43-2.36 (m, 4H), 2.15-1.89 (m, 2H), 0.94 (t, J=7 Hz, 3H).

3b) [5-cyclobutyl-3-(2,6-dichlorophenyl)-4-isoxazolyl]methanol

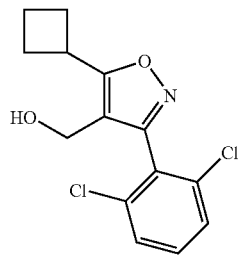

To a solution of ethyl 5-cyclobutyl-3-(2,6-dichlorophenyl)-4-isoxazolecarboxylate (1.5 g, 4.47 mmol) in tetrahydrofuran (20 mL) at 0° C. was added a 1.5 M solution of diisobutylaluminum hydride in toluene (6.3 mL, 9.39 mmol) slowly. The solution was allowed to warm slowly to ambient temperature and after 4 hours the solution was re-cooled to 0° C. and additional 1.5 M diisobutylaluminum hydride in toluene was added (6 mL, 9 mmol). The solution was allowed to stir with the flask in the ice bath for 1.5 h. Some aqueous Rochelle's salt was added dropwise followed by ethyl acetate. The mixture was stirred overnight and the phases were separated. The aqueous phase was extracted one more time with ethyl acetate. The combined organic phases were washed with Rochelle's salt, then brine, dried over MgSO$_4$ and concentrated in vacuo to yield a white solid. (1.3 g, 98%). $^1$H-NMR (DMSO-d$_6$,) δ 7.61-7.51 (m, 3H), 4.87 (t, J=5 Hz, 1H), 4.10 (d, J=5 Hz, 2H), 3.87 (quintet, J=9 Hz, 1H), 2.37-2.30 (m, 4H), 2.29-1.87 (m, 2H).

3c) Methyl 6-[4-({[5-cyclobutyl-3-(2,6-dichlorophenyl)-4-isoxazolyl]methyl}oxy)phenyl]-1-naphthalenecarboxylate

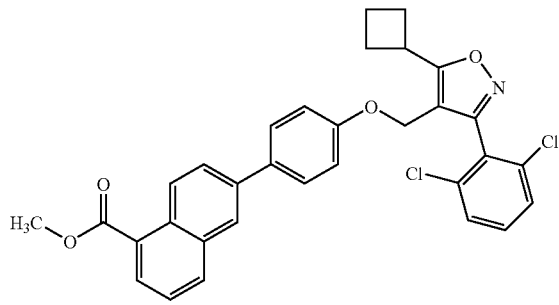

To a solution of [5-cyclobutyl-3-(2,6-dichlorophenyl)-4-isoxazolyl]methanol (150 mg, 0.503 mmol), methyl 6-(4-hydroxyphenyl)-1-naphthalenecarboxylate (140 mg, 0.503 mmol), triphenylphosphine (145 mg, 0.553 mmol) in dichloromethane (1.5 mL) was added diisopropyl azodicarboxylate (0.099 mL, 0.553 mmol) dropwise. The solution was heated in a microwave reactor at 100° C. for 10 minutes. The product was purified by chromatography (silica gel, 0-15% ethyl acetate in hexanes gradient elution) to afford a white solid (0.069 g, 25%). $^1$H-NMR (DMSO-d$_6$,) δ 8.77 (d, J=9 Hz, 1H), 8.23-8.20 (m, 2H), 8.09 (d, J=9 Hz, 1H), 7.93 (d, J=11 Hz, 1H), 7.70-7.51 (m, 6H), 6.90 (d, J=9 Hz, 2H), 4.83 (s, 2H), 4.00 (quintet, J=9 Hz, 1H), 3.92 (s, 3H), 2.43-2.31 (m, 4H), 2.10-1.92 (m, 2H). APCI-LCMS m/z 558 (M+H)$^+$.

3d) 6-[4-({[5-cyclobutyl-3-(2,6-dichlorophenyl)-4-isoxazolyl]methyl}oxy)phenyl]-1-naphthalenecarboxylic acid

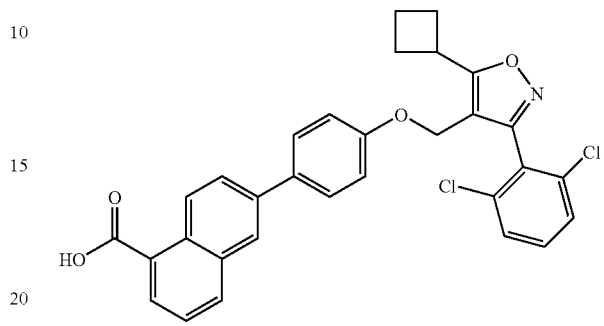

To a solution of methyl 6-[4-({[5-cyclobutyl-3-(2,6-dichlorophenyl)-4-isoxazolyl]methyl}oxy)phenyl]-1-naphthalenecarboxylate (65 mg, 0.116 mmol) in a 2:1 mixture of tetrahydrofuran and methanol (1.5 mL) was added 1N sodium hydroxide (0.175 mL, 0.175 mmol). The solution was heated in a microwave reactor at 120° C. for 500 seconds. The solution was concentrated and water was added followed by 0.175 mL of 1N HCl. The solution was extracted twice with ethyl acetate. The combined organic phases were washed one time with brine and concentrated. Ether was added and the solution was again concentrated to dryness to afford the title compound as a white solid (56 mg, 89%). $^1$H-NMR (DMSO-d$_6$,) δ 13.14 (s, 1H), 8.88 (d, J=9 Hz, 1H), 8.20-8.16 (m, 2H), 8.09 (d, J=9 Hz, 1H), 7.90 (d, J=9 Hz, 1H), 7.69-7.49 (m, 6H), 6.90 (d, J=9 Hz, 2H), 4.83 (s, 2H), 4.00 (quintet, J=9 Hz, 1H), 2.43-2.34 (m, 4H), 2.10-1.92 (m, 2H). HRMS C$_{31}$H$_{23}$Cl$_2$NO$_4$ m/z 544.10769 (M+H)$^+_{Cal}$; 544.10747 (M+H)$^+_{Obs}$.

EXAMPLE 4

6-[4-({[3-[(2,6-dichlorophenyl)methyl]-5-(1-methylethyl)-4-isoxazolyl]methyl}oxy)phenyl]-1-naphthalenecarboxylic acid

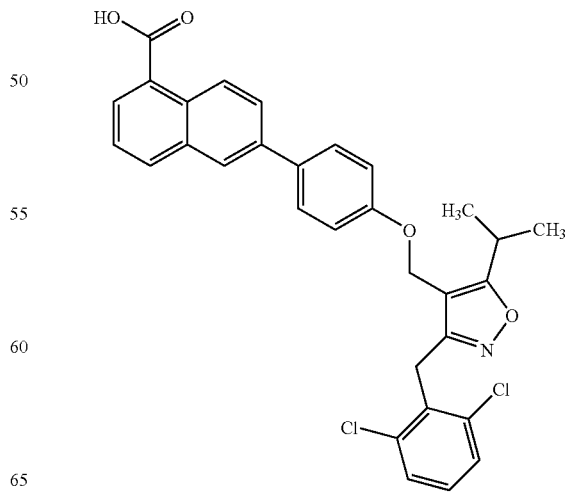

4a) 2-(2,6-dichlorophenyl)-N-hydroxyethanimidoyl chloride

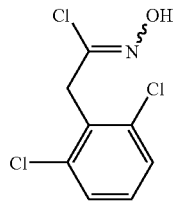

A solution of sodium hydroxide (0.672 g, 16.8 mmol) and hydroxylamine hydrochloride (1.17 g, 16.8 mmol) in water (11 mL) was added to a solution of (2,6-dichlorophenyl)acetaldehyde (2.78 g, 14.7 mmol) in ethanol (21 mL). The resulting solution was heated in an 83° C. oil bath overnight. The sample was concentrated and filtered. The resulting solid was dried with $P_2O_5$ in a vacuum oven at 45° C. under reduced pressure to provide the oxime as a mixture of isomers (2.21 g yield, 74%). A solution of (2,6-dichlorophenyl)acetaldehyde oxime (1.05 g, 4.82 mmol) in dimethylformamide (3.8 mL) was stirred as N-chlorosuccinimide (0.64 g, 4.82 mmol) was added and the resulting solution was allowed to stir for one hour. The solution was poured into water and extracted with ether. The organic layer was washed with brine, dried with magnesium sulfate, filtered and concentrated to yield the title compound (2.60 g, 77%). $^1$H NMR (DMSO-$d_6$): δ 11.78 (s, 1H), 7.47 (d, J=8 Hz, 2H), 7.33 (t, J=8 Hz, 1H), 4.08 (s, 2H).

4b) Methyl 3-[(2,6-dichlorophenyl)methyl]-5-(1-methylethyl)-4-isoxazolecarboxylate

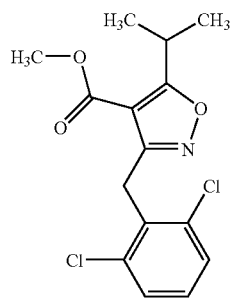

A solution of methyl isobutyrylacetate (1.93 g, 13.4 mmol) in tetrahydrofuran (2.7 mL) was stirred at 0° C. as 0.5 N sodium methoxide in methanol solution (27 mL, 13.5 mmol) was added. A solution of 2-(2,6-dichlorophenyl)-N-hydroxyethanimidoyl chloride (2.60 g, 11.18 mmol) in tetrahydrofuran (8.7 mL) was added and the solution was allowed to warm to room temperature and stir overnight. The mixture was concentrated then partitioned between water and ethyl acetate. The organic layer was dried with magnesium sulfate, filtered, and concentrated. The residue was purified by chromatography (silica gel, 0%-30% ethyl acetate in hexane) to provide the title compound (1.10 g, 30%). $^1$HNMR (DMSO-$d_6$): δ 7.48 (d, J=8 Hz, 2H), 7.34 (t, J=8 Hz, 1H), 4.42 (s, 2H), 3.84 (s, 3H), 3.68 (septet, J=7 Hz, 1H), 1.24 (d, J=7 Hz, 6H).

4c) [3-[(2,6-dichlorophenyl)methyl]-5-(1-methylethyl)-4-isoxazolyl]methanol

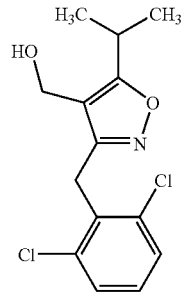

A solution of methyl 3-[(2,6-dichlorophenyl)methyl]-5-(1-methylethyl)-4-isoxazolecarboxylate (1.18 g, 3.6 mmol) (from multiple batches) in tetrahydrofuran (10 mL) was stirred at 0° C. as a 1.5 M solution of diisobutylaluminum hydride in toluene (3.7 mL, 5.6 mmol) was added. The solution was allowed to warm to room temperature and stir overnight. Methanol (0.27 mL) was added followed by water (2.7 mL) then 2 N sodium hydroxide (4 mL). The solution was filtered through celite. The filtrate was partitioned between ethyl acetate and water. An aqueous solution of Rochelle's salt was added. The organic layer was separated, dried with magnesium sulfate, concentrated and purified by chromatography (silica gel, 30% ethyl acetate in hexane) to provide the title compound (1.07 g, 99%). $^1$H NMR (DMSO-$d_6$): δ 7.46 (d, J=8 Hz, 2H), 7.32 (t, J=8 Hz, 1H), 5.01 (t, J=5 Hz, 1H), 4.36 (d, J=5 Hz, 2H), 4.22 (s, 2H), 3.21 (septet, J=7 Hz, 1H) 1.20 (d, J=7 Hz, 6H). ESI-LCMS m/z 300 (M+H)$^+$.

4d) Ethyl 6-hydroxy-1-naphthalenecarboxylate

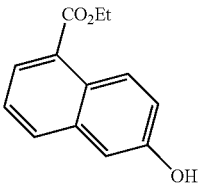

Thionyl chloride (2.3 mL, 31.9 mmol) was slowly added to a solution of 6-hydroxy-1-naphthoic acid (3 g, 15.9 mmol) in ethanol (140 mL) and stirred under $N_2$. After addition, the reaction mixture was heated at reflux under nitrogen for 6 days. The reaction mixture was cooled to room temperature and concentrated to give the crude product as an oil. The oil was carefully partitioned between 5% $NaHCO_3$ and EtOAc. The organic phase was separated and washed with brine, dried over $MgSO_4$, filtered and the filtrate was concentrated to give 3 g (87%) of the product as a red amorphous solid. $^1$H NMR (400 MHz, DMSO-$d_6$): δ 9.92 (s, 1 H), 8.57 (m, 1 H), 7.92 (d, J=8 Hz, 1 H), 7.85 (d, J=7 Hz, 1 H), 7.45 (t, J=8, 1 H), 7.20-7.18 (m, 2 H), 4.38-4.33 (m, 2 H), 1.34 (t, J=7 Hz, 3 H).

4e) Ethyl 6-{[(trifluoromethyl)sulfonyl]oxy}-1-naphthalenecarboxylate

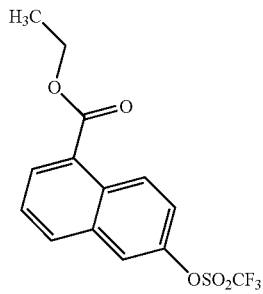

Ethyl 6-hydroxy-1-naphthalenecarboxylate (3 g, 13.9 mmol) was dissolved in $CH_2Cl_2$ (24 mL) and the solution was cooled to −5° C. with an acetone-ice bath. To the cold solution was added pyridine (7 mL, 83.2 mmol) with stirring under $N_2$. The reaction mixture was stirred at −5° C. for several minutes and triflic anhydride (2.8 mL, 16.6 mmol) was slowly added. The reaction mixture was stirred at 0° C. for 1 hr. The reaction mixture was quenched with water and extracted with ether. The organic phase was separated and washed with 1N HCl, followed by brine, dried with $MgSO_4$, filtered, and the filtrate was concentrated. The crude material was purified by flash chromatography over $SiO_2$ with a Hex:EtOAc (0 to 50% EtOAc) gradient to afford 3.9 g (81%) of the title compound as white crystals. $^1$H NMR (400 MHz, DMSO-$d_6$): δ 8.92 (d, J=10 Hz, 1 H), 8.33 (d, J=8 Hz, 1H), 8.28 (m, 1 H), 8.23 (d, J=7 Hz, 1 H), 7.77-7.72 (m, 2 H), 4.43-4.38 (m, 2 H), 1.36 (t, J=7 Hz, 3 H).

4f) Ethyl 6-(4-hydroxyphenyl)-1-naphthalenecarboxylate

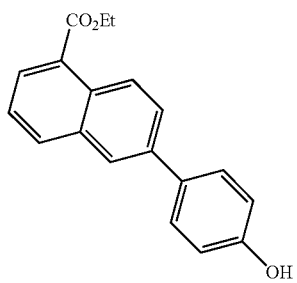

A solution of ethyl 6-{[(trifluoromethyl)sulfonyl]oxy}-1-naphthalenecarboxylate (0.3 g, 0.861 mmol), tetrakis(triphenylphosphine) palladium (0) (0.04 g, 0.0345 mmol), 2 M $Na_2CO_3$ (4 mL) and 4-hydroxyphenyl boronic acid (0.143 g, 1.03 mmol) in ethylene glycol dimethyl ether (5 mL) was heated at 80° C. for 1.5 h. The reaction mixture was cooled to room temperature, diluted with water and EtOAc. The EtOAc layer was separated, washed with brine, dried over $MgSO_4$, filtered, and the filtrate was concentrated to give the crude product as oil. The crude material was purified by flash chromatography over $SiO_2$ with a Hex:EtOAc (0 to 50% EtOAc) gradient to afford 0.23 g (92%) of the title compound as an oil. $^1$H NMR (400 MHz, DMSO-$d_6$): δ 9.63 (s, 1 H), 8.76 (d, J=9.0 Hz, 1 H), 8.20 (m, 2 H), 8.07 (d, J=7 Hz, 1H), 7.93 (m, 1 H), 7.66 (d, J =9 Hz, 2 H), 7.58 (t, J=8 Hz, 1 H), 6.88 (d, J=9 Hz, 2 H), 4.42-4.37 (m, 2 H), 1.37 (t, J =7 Hz, 3 H).

4g) Ethyl 6-[4-({[3-[(2,6-dichlorophenyl)methyl]-5-(1-methylethyl)-4-isoxazolyl]methyl}oxy)phenyl]-1-naphthalenecarboxylate

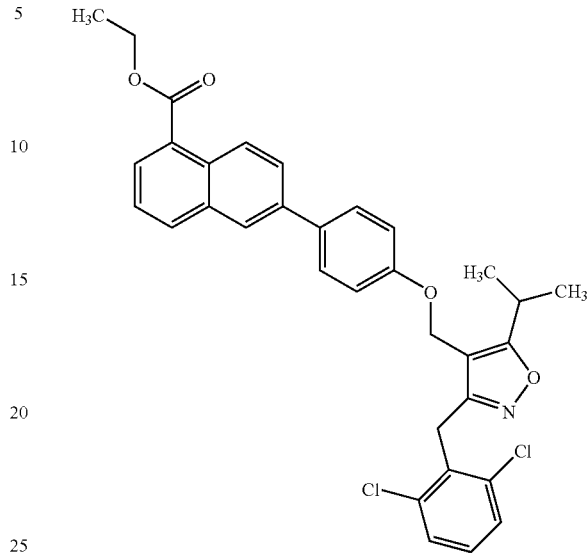

A solution of [3-[(2,6-dichlorophenyl)methyl]-5-(1-methylethyl)-4-isoxazolyl]methanol (0.105 g, 0.35 mmol), ethyl 6-(4-hydroxyphenyl)-1-naphthalenecarboxylate (0.102 g, 0.35 mmol), triphenylphosphine (0.092 g, 0.35 mmol) and diisopropyl azodicarboxylate (0.063 mL, 0.35 mmol) in toluene (3.5 mL) was placed in microwave reaction tube and heated to 80° C. for 500 seconds. The solution was concentrated and purified by chromatography (silica gel, hexane to 1:4 ethyl acetate: hexanes) to provide the title compound (0.126 g, 60.9% as 0.2 EtOAc). $^1$H NMR (DMSO-$d_6$): δ 8.79 (d, J=9 Hz, 1H), 8.28 (d, J=2 Hz, 1H), 8.23 (d, J=8 Hz, 1H), 8.09 (d, J=7 Hz, 1H), 7.98 (dd, J=2, 9 Hz, 1H), 7.81 (d, J=9 Hz, 2H), 7.61 (t, J=8 Hz, 1H), 7.46 (d, J=8 Hz, 2H), 7.32 (t, J=8 Hz, 1H), 7.16 (d, J=9 Hz, 2H), 5.08 (s, 2 H), 4.40 (q, J=7 Hz, 2 H), 4.29 (s, 2 H), 3.34 (septet, J=7 Hz, overlapping $H_2O$ 1 H), 1.37 (t, J=7 Hz, 3 H), 1.22 (d, J=7 Hz, 6 H). ESI-LCMS m/z 574 (M+H)$^+$.

4h) 6-[4-({[3-[(2,6-dichlorophenyl)methyl]-5-(1-methylethyl)-4-isoxazolyl]methyl}oxy)phenyl]-1-naphthalenecarboxylic acid

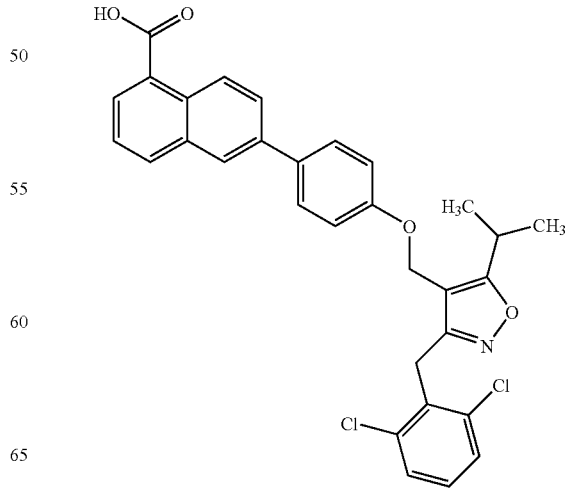

A solution of ethyl 6-[4-({[3-[(2,6-dichlorophenyl)methyl]-5-(1-methylethyl)-4-isoxazolyl]methyl}oxy)phenyl]-1-naphthalenecarboxylate (0.116 g, 0.20 mmol) in tetrahydrofuran (2 mL) was placed in a microwave reaction tube. Ethanol (1 mL) was added followed by 1N sodium hydroxide (0.312 mL, 0.31 mmol). The tube was sealed and heated in a microwave reactor to 100° C. for 500 seconds. Additional sodium hydroxide solution (0.2 mL, 0.2 mmol) was added and the solution was heated in a microwave reactor to 100° C. for another 500 seconds. The solution was neutralized with 1 N hydrochloric acid and concentrated. The residue was slurried in hexanes. The solid was slurried in water and the mixture was decanted and the solid dried to yield the title compound as a white solid (0.112 g, 100% as 0.15EtOAc). $^1$H NMR (DMSO-d$_6$) δ 13.14 (s, 1H), 8.91 (d, J=9 Hz, 1H), 8.26 (s, 1H), 8.20 (d, J=8 Hz, 1H), 8.10 (d, J=7 Hz, 1H), 7.96 (dd, J=2, 9 Hz, 1H), 7.80 (d, J=9 Hz, 2H), 7.58 (m, 1H), 7.46 (d, J=8 Hz, 2H), 7.31 (t, J=8 Hz, 1H), 7.16 (d, J=9 Hz, 2H), 5.08 (s, 2H), 4.29 (s, 2H), 3.36 (septet, J=7 Hz, overlapping H$_2$O 1H), 1.22 (d, J=7 Hz, 6H). HRMS C$_{31}$H$_{25}$NO$_4$Cl$_2$ m/z 546.1239 (M+H)$^+_{Cal}$; 546.1226 (M+H)$^+_{Obs}$.

EXAMPLE 5

6-[4-({[3-[2-(2,6-dichlorophenyl)ethyl]-5-(1-methylethyl)-4-isoxazolyl]methyl}oxy)phenyl]-1-naphthalenecarboxylic acid

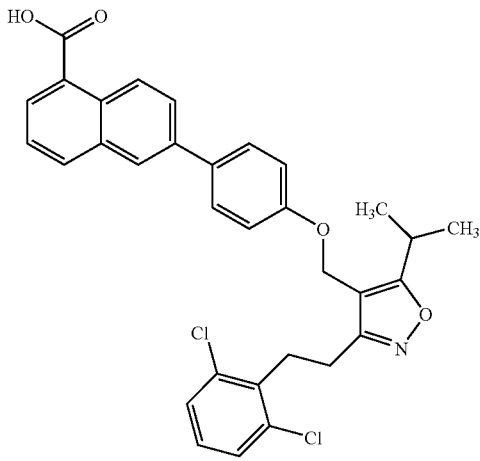

5a) 3-(2,6-dichlorophenyl)-1-propanol

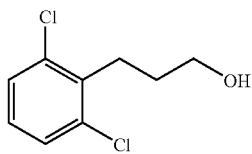

A solution of 3-(2,6-dichlorophenyl)propanoic acid (5.00 g, 22.8 mmol) in THF (114 mL) was stirred at room temperature as triethylamine (3.2 mL, 22.8 mmol) was added. The solution was then cooled in an ice/water bath before the addition of a 1 M solution of isopropylchloroformate in toluene (22.8 mL, 22.8 mmol). After 30 minutes the mixture was filtered into a mixture of sodium borohydride (1.13 g, 30 mmol) in water (8 mL). The resulting mixture was stirred in an ice/water bath and allowed to warm slowly to room temperature. The mixture was allowed to stir at room temperature overnight, then was filtered. The filtrate was partitioned between brine and ethyl acetate. The organic layer was dried with MgSO$_4$, filtered, and concentrated. The residue was purified by chromatography (silica gel, 3:7 ethyl acetate:hexanes) to provide the title compound (3.85 g, 77% as •0.17 EtOAc). $^1$H NMR (d$_6$-DMSO): δ 7.41 (d, J=8 Hz, 2H), 7.22 (t, J=8 Hz, 1H), 4.57 (t, J=5 Hz, 1H), 3.48-3.43 (m, 2H), 2.88-2.84 (m, 2H), 1.65-1.58 (m, 2H).

5b) (1E)-3-(2,6-dichlorophenyl)propanal oxime, (1Z)-3-(2,6-dichlorophenyl)propanal oxime

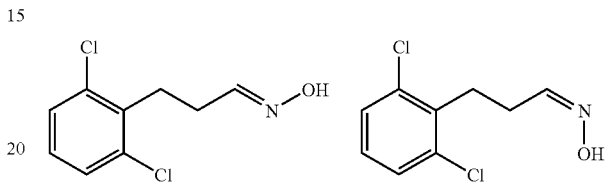

A solution of sulfurtrioxide•pyridine (7.57 g, 47.6 mmol) in DMSO (48 mL) was added to a solution of triethylamine (6.63 mL, 47.6 mmol), and 3-(2,6-dichlorophenyl)-1-propanol (3.25 g, 15.8 mmol) in dichloromethane (48 mL) in a ice/water bath. The solution was allowed to warm to room temperature and stir for 3.5 hours before being partitioned between brine and ether. The organic layer was washed with 10% aqueous citric acid, and then brine, before being dried with MgSO$_4$, filtered, and concentrated to provide the aldehyde (2.85 g, 89%). A solution of sodium hydroxide (0.728 g, 18.2 mmol) and hydroxylamine hydrochloride (1.26 g, 18.2 mmol) in water (12 mL) was added to a solution of the unpurified 3-(2,6-dichlorophenyl)propanal (2.85 g, 14 mmol) in ethanol (23 mL). The resulting solution was heated at 90° C. overnight. The sample was concentrated and the residue was partitioned between ethyl acetate and brine. The organic layer was dried with magnesium sulfate, filtered, and concentrated. The residue was purified by chromatography (silica gel, hexane to 1:4 ethyl acetate:hexanes) to provide the title compounds (1.06 g combined yield, 37%). $^1$H NMR (DMSO-d$_6$): higher R$_f$ geometric isomer δ 11.47 (s, 1H), 7.43 (d, J=8 Hz, 2H), 7.36 (t, J=6 Hz, 1H), 7.25 (t, J=8 Hz, 1H), 3.03-2.99 (m, 2H), 2.37-2.32 (m, 2H). lower R$_f$ geometric isomer 10.86 (s, 1H), 7.43 (d, J=8 Hz, 2H), 7.25 (t, J=8 Hz, 1H), 6.74 (t, J=5 Hz, 1H), 3.02-2.98 (m, 2H), 2.51-2.46 (m, overlapping DMSO, 2H).

5c) 3-(2,6-dichlorophenyl)-N-hydroxypropanimidoyl chloride

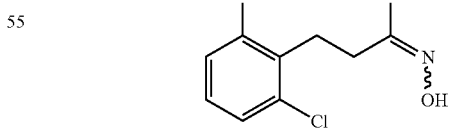

A solution of 3-(2,6-dichlorophenyl)propanal oxime (1.05 g, 4.82 mmol) in dimethylformamide (3.8 mL) was stirred as N-chlorosuccinimide (0.64 g, 4.82 mmol) was added. The resulting solution was allowed to stir for one hour. The solution was poured into water and extracted with ether. The organic layer was washed with brine, dried with magnesium sulfate, filtered and concentrated to yield the title compound (1.05 g, 86%). ¹H NMR (DMSO-d₆): δ 11.67 (s, 1H), 7.45 (d, J=8 Hz, 2H), 7.28 (t, J=8 Hz, 1H), 3.17-3.13 (m, 2H), 2.68-2.64 (m, 2H).

5d) Methyl 3-[2-(2,6-dichlorophenyl)ethyl]-5-(1-methylethyl)-4-isoxazolecarboxylate

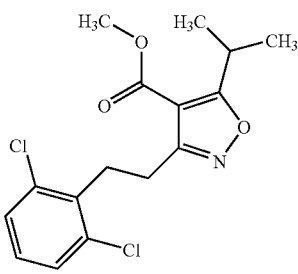

A solution of methyl isobutyrylacetate (0.662 g, 5.8 mmol) in tetrahydrofuran (1.16 mL) was stirred at 0° C. as 0.5 N sodium methoxide in methanol solution (11.6 mL, 5.8 mmol) was added. A solution of 3-(2,6-dichlorophenyl)-N-hydroxypropanimidoyl chloride (1.04 g, 4.82 mmol) in tetrahydrofuran (3.8 mL) was added and the solution was allowed to warm to room temperature and was stirred overnight. The mixture was concentrated and the residue triturated with water and filtered to yield a white solid which was dried in a 45° C. oven with P₂O₅ under reduced pressure to yield the title compound (0.926 g, 56%).

¹H NMR (DMSO-d₆): δ 7.43 (d, J=8 Hz, 2H), 7.25 (t, J=8 Hz, 1H), 3.73 (s, 3H), 3.67 (septet, J=7 Hz, 1H), 3.24-3.20 (m, 2H), 3.07-3.03 (m, 2H), 1.23 (d, J=7 Hz, 6H).

5e) [3-[2-(2,6-dichlorophenyl)ethyl]-5-(1-methylethyl)-4-isoxazolyl]methanol

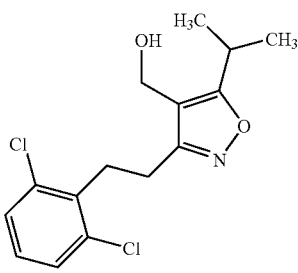

A solution of methyl 3-[2-(2,6-dichlorophenyl)ethyl]-5-(1-methylethyl)-4-isoxazolecarboxylate (0.900 g, 2.63 mmol) in THF (7.3 mL) was stirred at 0° C. as a 1.5M solution of diisobutylaluminum hydride in toluene (3.7 mL, 5.6 mmol) was added. The solution was allowed to warm to room temperature and stir overnight. Additional diisobutylaluminum hydride in toluene (1.8 mL, 2.7 mmol) was added and the solution was allowed to stir for another 3 hours. Methanol was added followed by a saturated aqueous solution of Rochelle's salt. The solution was stirred for two hours then was partitioned between ethyl acetate and brine. The organic layer was dried with magnesium sulfate, concentrated and purified by chromatography (silica gel, 0-60% ethyl acetate in hexane) to provide the title compound (0.80 g, 51.6% as 0.25EtOAc). ¹H NMR (DMSO-d₆): δ 7.45 (d, J=8 Hz, 2H), 7.28 (t, J=8 Hz, 1H), 4.89 (t, J=5 Hz, 1H), 4.26 (d, J=5 Hz, 2H), 3.31-3.18 (m, 3H), 2.83-2.79 (m, 2H), 1.21 (d, J=7 Hz, 6H).

5f) Ethyl 6-[4-({[3-[2-(2,6-dichlorophenyl)ethyl]-5-(1-methylethyl)-4-isoxazolyl]methyl}oxy)phenyl]-1-naphthalenecarboxylate

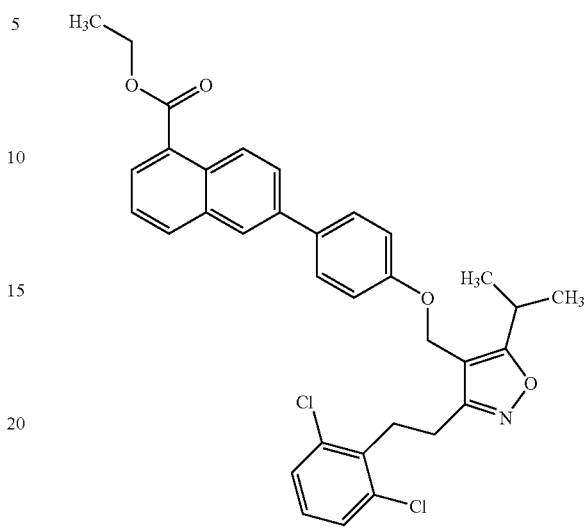

A solution of [3-[2-(2,6-dichlorophenyl)ethyl]-5-(1-methylethyl)-4-isoxazolyl]methanol (0.110 g, 0.35 mmol) (from multiple batches), ethyl 6-(4-hydroxyphenyl)-1-naphthalenecarboxylate (0.102 g, 0.35 mmol), triphenylphosphine (0.092 g, 0.35 mmol) and diisopropyl azodicarboxylate (0.063 mL, 0.35 mmol) in toluene (3.5 mL) was placed in microwave reaction tube and heated to 80° C. for 1000 seconds. The solution was concentrated and purified by chromatography (silica gel, hexane to 1:4 ethyl acetate:hexanes) to provide the title compound (0.115 g, 51.6% as 0.7EtOAc). ¹H NMR (DMSO-d₆): δ 8.79 (d, J=9 Hz, 1H), 8.28 (s, 1H), 8.22 (d, J=8 Hz, 1H), 8.09 (d, J=7 Hz, 1H), 7.98 (dd, J=2, 9 Hz, 1H), 7.80 (d, J=9 Hz, 2H), 7.60 (m, 1H), 7.42 (d, J=8 Hz, 2H), 7.25 (t, J=8 Hz, 1H), 7.14 (d, J=8 Hz, 2H), 4.98 (s, 2H), 4.40 (q, J=7 Hz, 2H), 3.35 (septet, J=7 Hz, overlapping H₂O, 1H), 3.24-3.20 (m, 2H), 2.89-2.85 (m, 2H), 1.37 (t, J=7 Hz, 3H), 1.25 (d, J=7 Hz, 6H). ESI-LCMS m/z 588 (M+H)⁺.

5g) 6-[4-({[3-[2-(2,6-dichlorophenyl)ethyl]-5-(1-methylethyl)-4-isoxazolyl]methyl}oxy)phenyl]-1-naphthalenecarboxylic acid

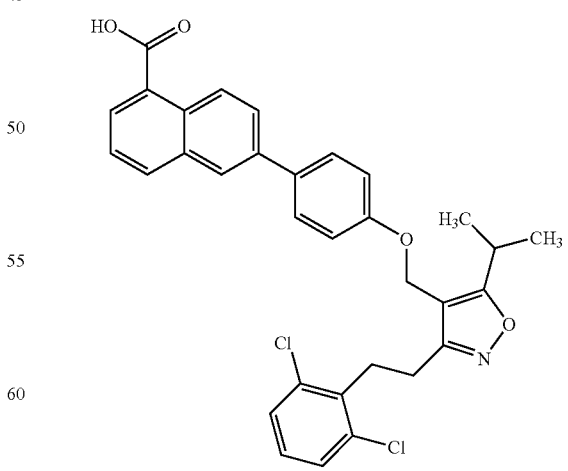

A solution of ethyl 6-[4-({[3-[2-(2,6-dichlorophenyl)ethyl]-5-(1-methylethyl)-4-isoxazolyl]methyl}oxy)phenyl]-1-naphthalenecarboxylate (0.110 g, 0.187 mmol) in tetrahydrofuran (2 mL) was placed in a microwave reaction tube.

Ethanol (1 mL) was added followed by 1 N sodium hydroxide (0.36 mL, 0.36 mmol). The tube was sealed and heated in a microwave reactor to 100° C. for 500 seconds. Additional sodium hydroxide solution (0.2 mL, 0.2 mmol) was added and the solution was heated in a microwave reactor to 100° C. for another 500 seconds. The solution was neutralized and concentrated. The residue was partitioned between water and ethyl acetate. The organic layer was concentrated to yield the title compound as a white solid (0.088 g, 83.8%). $^1$H NMR (DMSO-$d_6$): δ 13.14 (s, 1H), 8.91 (d, J=9 Hz, 1H), 8.27 (d, J=1 Hz, 1H), 8.20 (d, J=8 Hz, 1H), 7.96 (dd, J=2, 9 Hz, 2H), 7.80 (d, J=9 Hz, 2H), 7.58 (m, 1H), 7.43 (d, J=8 Hz, 2H), 7.26 (m, 1H), 7.15 (d, J=9 Hz, 2H), 4.98 (s, 2H), 3.35 (septet, J=7 Hz, overlapping H$_2$O, 1H), 3.25-3.20 (m, 2H), 2.89-2.85 (m, 2H), 1.25 (d, J=7 Hz, 6H).

HRMS $C_{32}H_{27}NO_4Cl_2$ m/z 560.1395 $(M+H)^+_{Cal}$; 560.1409 $(M+H)^+_{Obs}$.

EXAMPLE 6

6-(4-{[3-(2,6-dichlorophenyl)-5-isopropylisoxazol-4-yl]methoxy}phenyl)-2-naphthoic acid

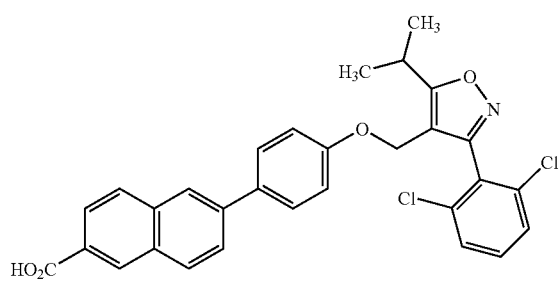

6a) Methyl 6-(4-hydroxyphenyl)-2-naphthoate

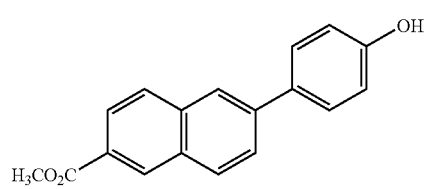

To a solution of methyl 6-bromo-2-naphthoate (150 mg, 0.57 mmol), 4-(4,4,5,5-tetramethyl-1,3,2-dioxaborolan-2-yl)phenol (150 mg, 0.68 mmol), and 2.0 M Na$_2$CO$_3$ (1.10 mL, aq) in dimethoxyethane (5 mL) was added [1,1'-bis(diphenylphosphino)ferrocene]dichloropalladium (14 mg, 0.02 mmol) and the mixture stirred at 70° C. for 20 min. The mixture was diluted with 25 mL of EtOAc then filtered through a plug of Celite and silica gel. The filtrate was washed with H$_2$O, then brine, dried over Na$_2$SO$_4$, then concentrated and purified by silica gel chromatography (40 g of silica gel eluting with 0-50% EtOAc in hexanes over 45 minutes) to give methyl 6-(4-hydroxyphenyl)-2-naphthoate as a beige solid (55 mg, 35%.) $^1$H NMR (DMSO-$d_6$): δ 9.67 (s, 1H), 8.60 (s, 1 H), 8.17-8.13 (m, 2 H), 8.02 (d, J=9 Hz, 1 H), 7.95 (d, J=9 Hz, 1 H), 7.87 (d, J=9 Hz, 1H), 7.67 (d, J=8 Hz, 2H), 6.89 (d, J=8 Hz, 2H), 3.89 (s, 3H). ESI-LCMS m/z 279 $(M+H)^+$.

6b) 6-(4-{[3-(2,6-dichlorophenyl)-5-isopropylisoxazol-4-yl]methoxy}phenyl)-2-naphthoic acid

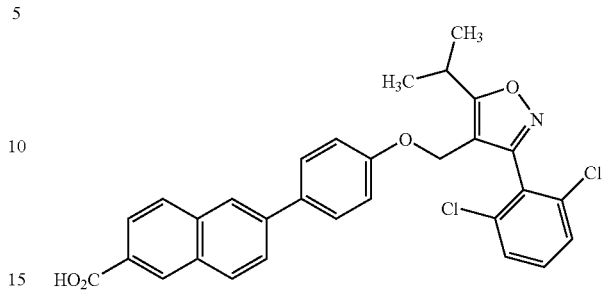

To solution of methyl 6-(4-hydroxyphenyl)-2-naphthoate (55 mg, 0.20 mmol) in DMF (1.0 mL) was added K$_2$CO$_3$ (68 mg, 0.49 mmol) and 4-(chloromethyl)-3-(2,6-dichlorophenyl)-5-isopropylisoxazole (91 mg, 0.30 mmol) and the mixture was stirred at ambient temperature for 12 hr. Additional 4-(chloromethyl)-3-(2,6-dichlorophenyl)-5-isopropylisoxazole (50 mg, 0.16 mmol) and K$_2$CO$_3$ (68 mg, 0.49 mmol) in DMF (0.5 mL) was added and the mixture stirred at 70° C. for 3 hr. The solution was diluted with 50 mL EtOAc then washed with three 25 mL portions of H$_2$O followed by 25 mL of brine then dried over Na$_2$SO$_4$, filtered, concentrated, and purified by silica gel chromatography (12 g of silica gel eluting with 0-40% EtOAc in hexanes over 45 minutes.) Product fractions were pooled and concentrated. To this residue was added EtOH (2.5 mL), THF (1.0 mL), H$_2$O (0.5 mL) and NaOH (35 mg, 0.84 mmol) and the solution was stirred at 60° C. for 12 hr. The solution was concentrated to ~⅓ volume then added dropwise to 1.0 N HCl (6 mL, aq.) The resulting solids were collected by suction filtration, washed with H$_2$O and dried to give the title compound as an off-white solid (42 mg, 94%.) $^1$H NMR (DMSO-$d_6$): δ 13.0 (broad s, 1H), 8.57 (s, 1H), 8.18 (s, 1H), 8.12 (d, J=9 Hz, 1H), 8.01 (d, J=9 Hz, 1H), 7.95 (d, J=9 Hz, 1H), 7.85 (d, J=9 Hz, 1H), 7.69 (d, J=8 Hz, 2H), 7.62 (d, J=8 Hz, 2H), 7.59-7.51 (m, 1H), 6.91 (d, J=8 Hz, 2H), 4.87 (s, 2 H), 3.45 (septet, J=7 Hz, 1H), 1.33 (d, J=7 Hz, 6H). ESI-LCMS m/z 532 $(M+H)^+$.

EXAMPLE 7

Methyl 6-[4-({[3-[2-(2,6-dichlorophenyl)ethyl]-5-(1-methylethyl)-4-isoxazolyl]methyl}oxy)phenyl]-2-naphthalenecarboxylate

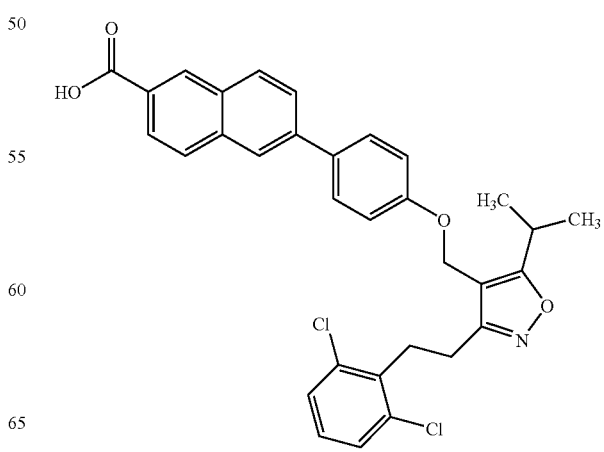

7a) Methyl 6-[4-({[3-[2-(2,6-dichlorophenyl)ethyl]-5-(1-methylethyl)-4-isoxazolyl]methyl}oxy)phenyl]-2-naphthalenecarboxylate

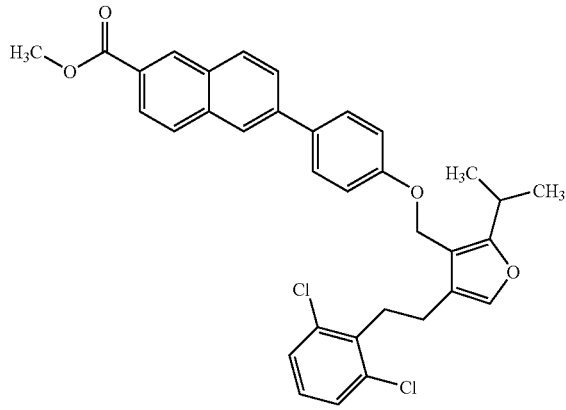

A solution of [3-[2-(2,6-dichlorophenyl)ethyl]-5-(1-methylethyl)-4-isoxazolyl]methanol (0.085 g, 0.27 mmol), methyl 6-(4-hydroxyphenyl)-2-naphthalenecarboxylate (0.075 g, 0.27 mmol), triphenyl phosphine (0.071 g, 0.27 mmol) and diisopropyl azodicarboxylate (0.049 mL, 0.27 mmol) in toluene (2.7 mL) was placed in microwave reaction tube and heated to 80° C. for 1000 seconds. The solution was concentrated and the residue dissolved in a solution of ethyl acetate and methanol, filtered and concentrated. The filtrate was purified by chromatography (silica gel, hexane to 3:7 ethyl acetate:hexanes) to provide the title compound (0.038 g, 24.5%). $^1$H NMR (DMSO-$d_6$): δ 8.62 (s, 1H), 8.25 (s, 1H), 8.18 (d, J=9 Hz, 1H), 8.06 (d, J=9 Hz, 1H), 7.97 (dd, J=1, 9 Hz, 1H), 7.92 (dd, J=2, 9 Hz, 1H), 7.81 (d, J=9 Hz, 2H), 7.42 (d, J=8 Hz, 2H), 7.25 (t, J=8 Hz, 1H), 7.14 (d, J=9 Hz, 2H), 4.99 (s, 2H), 3.90 (s, 3H), 3.35 (septet, J=7 Hz, overlapping H$_2$O 1H), 3.24-3.20 (m, 2H), 2.89-2.85 (m, 2H), 1.25 (d, J=7 Hz, 6H). ESI-LCMS m/z 574 (M+H)$^+$.

7b) 6-[4-({[3-[2-(2,6-dichlorophenyl)ethyl]-5-(1-methylethyl)-4-isoxazolyl]methyl}oxy)phenyl]-2-naphthalenecarboxylic acid

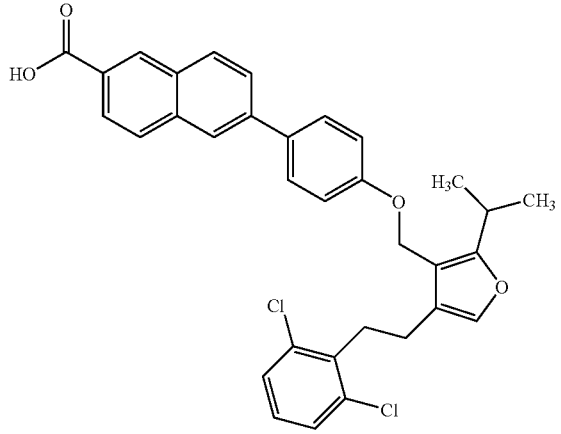

A solution of methyl 6-[4-({[3-[2-(2,6-dichlorophenyl)ethyl]-5-(1-methylethyl)-4-isoxazolyl]methyl}oxy)phenyl]-2-naphthalenecarboxylate (0.035 g, 0.061 mmol) in tetrahydrofuran (0.6 mL) was placed in a microwave reaction tube. Methanol (0.3 mL) was added followed by 1N sodium hydroxide (0.092 mL, 0.092 mmol). The tube was sealed and heated in a microwave reactor to 100° C. for 600 seconds. The solution was neutralized and concentrated. Water was added and the mixture was filtered. The resulting solid was dried in a vacuum oven at 45° C. with P$_2$O$_5$ to yield the title compound (0.027 g, 77.1%) $^1$H NMR (DMSO-$d_6$): δ 13.03 (s, 1H), 8.58 (s, 1H), 8.24 (s, 1H), 8.15 (d, J=9 Hz, 1H), 8.03 (d, J=9 Hz, 1H), 7.96 (dd, J=2, 9 Hz, 1H), 7.90 (dd, J=2, 9 Hz, 1H), 7.81 (d, J=9 Hz, 2H), 7.42 (d, J=8 Hz, 2H), 7.25 (m, 1H), 7.14 (d, J=9 Hz, 2H), 4.98 (s, 2H), 3.35 (septet, J=7 Hz, overlapping H$_2$O, 1H), 3.24-3.20 (m, 2H), 2.89-2.85 (m, 2H), 1.25 (d, J=7 Hz, 6H). HRMS C$_{32}$H$_{27}$NO$_4$Cl$_2$ m/z 560.1395 (M+H)$^+_{cal}$; 560.1409 (M+H)$^+_{Obs}$.

EXAMPLE 8

7-[4-({[3-(2,6-dichlorophenyl)-5-(1-methylethyl)-4-isoxazolyl]methyl}oxy)phenyl]-2-naphthalenecarboxylic acid

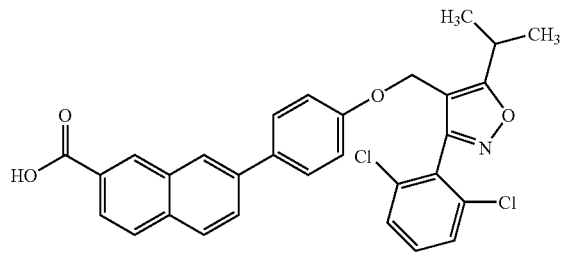

8a) Methyl 7-{[(trifluoromethyl)sulfonyl]oxy}-2-naphthalenecarboxylate

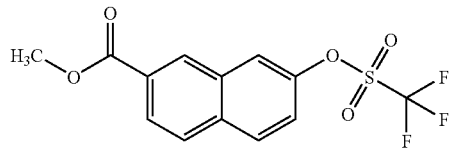

A solution of methyl 7-hydroxy-2-naphthalenecarboxylate (0.53 g, 2.62 mmol) in methylene chloride (6.6 mL) was stirred in an ice/acetone bath as pyridine (1.25 mL) was added followed by trifluoromethanesulfonic anhydride (0.53 mL, 3.12 mmol). The solution was allowed to stir for 1.5 hours before being partitioned between water and ether. The organic layer was washed with 1.0 N HCl, then brine, before being dried with magnesium sulfate, filtered and concentrated. The residue was purified by chromatography on silica gel, (hexane to 3:17 ethyl acetate:hexanes) to provide the title compound (0.40 g, 46%). $^1$H NMR (DMSO-$d_6$): δ 8.79 (s, 1H), 8.41 (d, J=2 Hz, 1H), 8.23 (d, J=7 Hz, 1H), 8.16 (d, J=9 Hz, 1H), 8.09-8.06 (m, 1H), 7.78-7.75 (m, 1H), 3.91 (s, 3H).

8b) Methyl 7-(4-hydroxyphenyl)-2-naphthalenecarboxylate

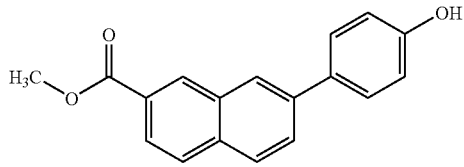

A solution of methyl 7-{[(trifluoromethyl)sulfonyl]oxy}-2-naphthalenecarboxylate (100 mg, 0.3 mmol), tetrakistriphenylphosphine palladium (14 mg, 0.012 mmol) and 4-(4,4,5,5-tetramethyl 1,3,2-dioxaborolan-2-yl-) phenol (79 mg, 0.36 mmol) in a mixture of dimethoxyethane (1.6 mL) and 2 M aqueous Na$_2$CO$_3$ (1.3 mL) was heated in a 70° C. oil bath for one hour. The solution was partitioned between ethyl acetate and water. The organic layer was dried with magnesium sulfate, filtered, and concentrated. The crude material was purified by chromatography on silica gel, (hexane to 3:7 ethyl acetate:hexanes) to provide the title compound (0.085 g, 95.5% as 0.20 ethyl acetate). $^1$H NMR (DMSO-d$_6$): δ 9.64 (s, 1H), 8.65 (s, 1H), 8.31 (s, 1H), 8.03-7.99 (m, 2H), 7.93-7.90 (m, 2H), 7.66 (d, J=9 Hz, 2H), 6.88 (d, J=9 Hz, 2H), 3.90 (s, 3H).

8c) Methyl 7-[4-({[3-(2,6-dichlorophenyl)-5-(1-methylethyl)-4-isoxazolyl]methyl}oxy)phenyl]-2-naphthalenecarboxylate

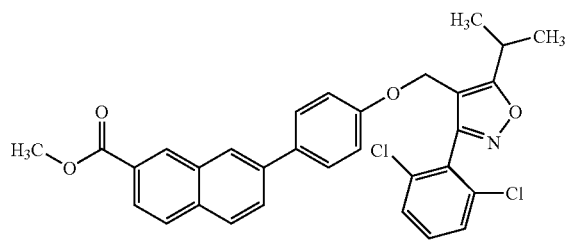

A solution of 4-(chloromethyl)-3-(2,6-dichlorophenyl)-5-(1-methylethyl)isoxazole (0.12 g, 0.36 mmol), methyl 7-(4-hydroxyphenyl)-2-naphthalenecarboxylate (0.084 g, 0.30 mmol), and cesium carbonate (137 mg, 0.42 mmol) in dimethylformamide (0.73 mL) was heated to 65° C. for 3 hours. The solution was partitioned between ethyl acetate and water. The organic layer was dried with magnesium sulfate, filtered and concentrated. The filtrate was purified by chromatography (silica gel, hexane to 3:7 ethyl acetate:hexanes) to provide the title compound (0.130 g, 68.4% as 1.0 ethyl acetate). $^1$H NMR (DMSO-d$_6$): δ 8.66 (s, 1H), 8.34 (s, 1H), 8.04-8.00 (m, 2H), 7.94-7.90 (m, 2H), 7.69 (d, J=9 Hz, 2H), 7.62 (d, J=8 Hz, 2H), 7.55-7.51 (m, 1H), 6.91 (d, J=9 Hz, 2H), 4.87 (s, 2H), 3.90 (s, 3H), 3.46 (septet, J=7 Hz, 1H), 1.33 (d, J=7 Hz, 6H). ESI-LCMS m/z 546 (M+H)$^+$.

8d) 7-[4-({[3-(2,6-dichlorophenyl)-5-(1-methylethyl)-4-isoxazolyl]methyl}oxy)phenyl]-2-naphthalenecarboxylic acid

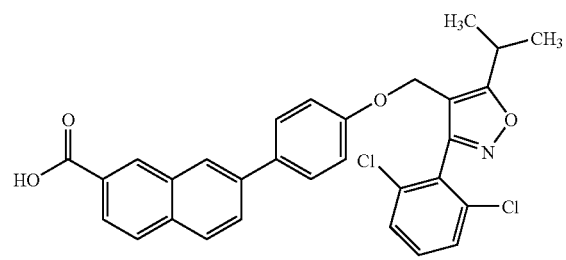

A solution of methyl 7-[4-({[3-(2,6-dichlorophenyl)-5-(1-methylethyl)-4-isoxazolyl]methyl}oxy)phenyl]-2-naphthalenecarboxylate (0.126 g, 0.2 mmol) in tetrahydrofuran (2.0 mL) was placed in a microwave reaction tube. Methanol (1.0 mL) was added followed by 1 N sodium hydroxide (0.3 mL, 0.3 mmol). The tube was sealed and heated in a microwave reactor to 100° C. for 600 seconds. The solution was neutralized and concentrated. Water was added and the mixture was filtered. The resulting solid was dried in a vacuum oven at 45° C. with P$_2$O$_5$ to yield the title compound (0.082 g, 73.9% as 0.30 tetrahydrofuran) $^1$H NMR (DMSO-d$_6$): δ 13.3-12.6 (broad s, approximately 1H), 8.61 (s, 1H), 8.29 (s, 1H), 8.02-7.87 (m, 4H), 7.68 (d, J=9 Hz, 2H), 7.62 (d, J=8 Hz, 2H), 7.54 (dd, J=7, 9 Hz, 1H), 6.91 (d, J=9 Hz, 2H), 4.86 (s, 2H), 3.44 (septet, J=7 Hz, overlapping H$_2$O, 1H), 1.33 (d, J=7 Hz, 6H). HRMS C$_{30}$H$_{23}$NO$_4$Cl$_2$ m/z 532.1082, (M+H)$^+_{cal}$; 532.1087 (M+H)$^+_{Obs}$.

EXAMPLE 9

7-[4-({[3-[2-(2,6-dichlorophenyl)ethyl]-5-(1-methylethyl)-4-isoxazolyl]methyl}oxy)phenyl]-2-naphthalenecarboxylic acid

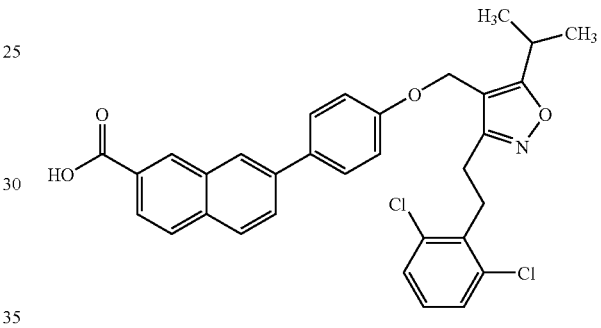

9a) Methyl 7-[4-({[3-[2-(2,6-dichlorophenyl)ethyl]-5-(1-methylethyl)-4-isoxazolyl]methyl}oxy)phenyl]-2-naphthalenecarboxylate

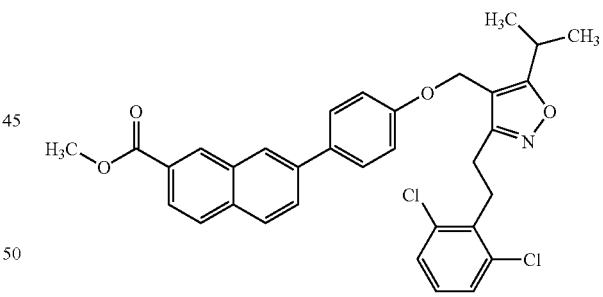

A solution of [3-[2-(2,6-dichlorophenyl)ethyl]-5-(1-methylethyl)-4-isoxazolyl]methanol (0.050 g, 0.16 mmol), methyl 7-(4-hydroxyphenyl)-2-naphthalenecarboxylate (0.045 g, 0.16 mmol), triphenyl phosphine (0.042 g, 0.16 mmol) and diisopropyl azodicarboxylate (0.043 mL, 0.16 mmol) in dichloromethane (1.6 mL) was placed in microwave reaction tube and heated to 80° C. for 20 minutes. The solution was concentrated and the residue was purified by chromatography (silica gel, hexane to 3:7 ethyl acetate:hexanes) to provide the title compound (0.059 g, 64%). $^1$H NMR (DMSO-d$_6$): δ 8.68 (s, 1H), 8.40 (s, 1H), 8.07-7.93 (m, 4H), 7.80 (d, J=7 Hz, 2H), 7.42 (d, J=8 Hz, 2H), 7.28-7.24 (m, 1H), 7.14 (d, J=7 Hz, 2H), 4.99 (s, 2H), 3.91 (s, 3H), 3.32-3.20 (2 m, overlapping H$_2$O, total 3H), 2.89-2.85 (m, 2H), 1.25 (d, J=7 Hz, 6H). ESI-LCMS m/z 574 (M+H)$^+$.

9b) 7-[4-({[3-[2-(2,6-dichlorophenyl)ethyl]-5-(1-methylethyl)-4-isoxazolyl]methyl}oxy)phenyl]-2-naphthalenecarboxylic acid

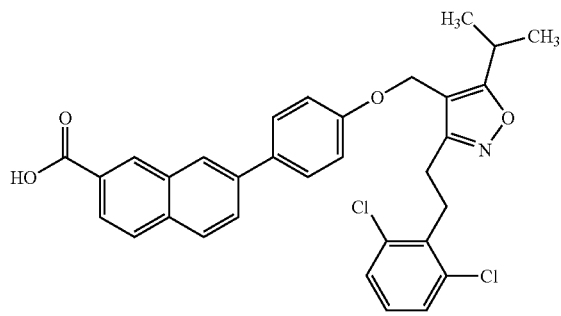

A solution of methyl 7-[4-({[3-[2-(2,6-dichlorophenyl)ethyl]-5-(1-methylethyl)-4-isoxazolyl]methyl}oxy)phenyl]-2-naphthalenecarboxylate (0.057 g, 0.1 mmol) in tetrahydrofuran (1.0 mL) was placed in a microwave reaction tube. Methanol (0.5 mL) was added followed by 1 N sodium hydroxide (0.15 mL, 0.15 mmol). The tube was sealed and heated in a microwave reactor to 100° C. for 600 seconds. The solution was neutralized and concentrated. Water was added and the mixture was filtered. The resulting solid was dried in a vacuum oven at 45° C. with $P_2O_5$ to yield the title compound (0.048 g, 76% as 0.20 tetrahydrofuran) $^1$H NMR (DMSO-$d_6$) δ 13.4-12.8 (broad s, approximately 1H), 8.59 (s, 1H), 8.31 (s, 1H), 8.01 (d, J=9 Hz, 1H) 7.94-7.90 (m, 3H), 7.79 (d, J=8 Hz, 2H), 7.43 (d, J=8 Hz, 2H), 7.28-7.24 (m, 1H), 7.14 (d, J=8 Hz, 2H), 4.98 (s, 2H), 3.39-3.21 (2m, overlapping $H_2O$, total 3H), 2.89-2.85 (m, 2H), 1.25 (d, J=7 Hz, 6H). HRMS $C_{32}H_{27}NO_4Cl_2$ m/z 560.1395 $(M+H)^+_{Cal}$; 560.1409 $(M+H)^+_{Obs}$.

EXAMPLE 10

7-[4-({[3-(2,6-dichlorophenyl)-5-(1-methylethyl)-4-isoxazolyl]methyl}oxy)phenyl]-1-naphthalenecarboxylic acid

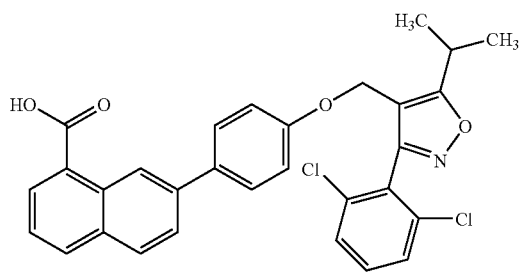

10a) Methyl 7-{[(trifluoromethyl)sulfonyl]oxy}-1-naphthalenecarboxylate

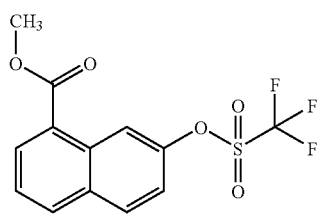

A solution of methyl 7-hydroxy-1-naphthalenecarboxylate (1.68 g, 8.34 mmol) in methylene chloride (21 mL) was stirred in an ice/acetone bath as pyridine (4.1 mL) was added followed by trifluoromethanesulfonic anhydride (1.7 mL, 10 mmol). The solution was allowed to stir for 1.5 hours before being partitioned between water and ether. The organic layer was washed with 1.0 N HCl, then brine, before being dried with magnesium sulfate, filtered and concentrated. The residue was purified by chromatography on silica gel (hexane to 1:9 ethyl acetate:hexanes) to provide the title compound (2.60 g, 93.2%).
$^1$H NMR (DMSO-$d_6$): δ 8.92 (d, J=2 Hz, 1H), 8.35-8.32 (m, 2H), 8.28 (d, J=9 Hz, 1H), 7.76-7.72 (m, 2H), 3.93 (s, 3H).

10b) Methyl 7-(4-hydroxyphenyl)-1-naphthalenecarboxylate

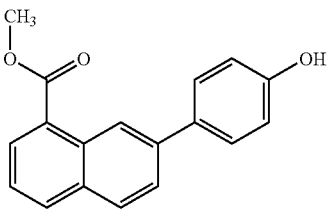

A solution of methyl 7-{[(trifluoromethyl)sulfonyl]oxy}-1-naphthalenecarboxylate (1.00 g, 3.0 mmol), tetrakistriphenylphosphine palladium (142 mg, 0.12 mmol) and 4-(4,4,5,5-tetramethyl 1,3,2-dioxaborolan-2-yl-) phenol (799 mg, 3.6 mmol) in a mixture of 1,2-dimethoxyethane (16 mL) and 2M aqueous $Na_2CO_3$ (13 mL) was heated in a 70° C. oil bath for 90 minutes. The solution was partitioned between ethyl acetate and water. The organic layer was dried with magnesium sulfate, filtered, and concentrated. The crude material was purified by chromatography on silica gel, hexane to 3:7 ethyl acetate:hexanes, to provide the title compound (0.648 g, 77.7%). $^1$H NMR (DMSO-$d_6$): δ 9.65 (s, 1H), 8.94 (s, 1H), 8.18-8.13 (m, 2H), 8.05 (d, J=8 Hz, 1H), 7.85 (dd, J=2, 9 Hz; 1H), 7.60 (d, J=9 Hz, 2H), 7.56-7.53 (m, 1H), 6.90 (d, J=9 Hz, 2H), 3.93 (s, 3H).

10c) Methyl 7-[4-({[3-(2,6-dichlorophenyl)-5-(1-methylethyl)-4-isoxazolyl]methyl}oxy)phenyl]-1-naphthalenecarboxylate

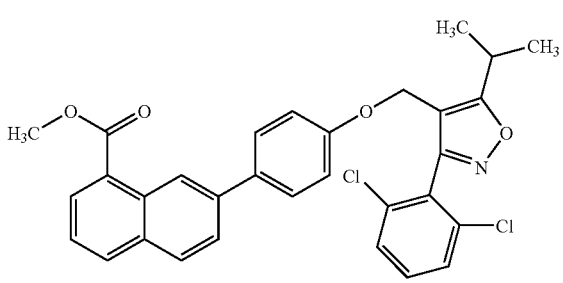

A solution of 4-(chloromethyl)-3-(2,6-dichlorophenyl)-5-(1-methylethyl)isoxazole (0.11 g, 0.36 mmol), methyl 7-(4-hydroxyphenyl)-1-naphthalenecarboxylate (0.083 g, 0.30 mmol), and cesium carbonate (137 mg, 0.42 mmol) in dimethylformamide (0.73 mL) was heated to 65° C. for 3 hours. The solution was partitioned between ethyl acetate and water. The organic layer was dried with magnesium sulfate, filtered, and concentrated. The filtrate was purified by chromatography (silica gel, hexane to 1:4 ethyl acetate:hexanes) to provide the title compound (0.123 g, 75%). $^1$H NMR (DMSO-$d_6$): δ 8.93 (s, 1H), 8.19-8.14 (m, 2H), 8.07 (d, J=9 Hz, 1H), 7.84 (dd, J=2, 9 Hz; 1H), 7.63 (d, J=8 Hz, 4H), 7.59-7.52 (m, 2H), 6.93 (d, J=9 Hz, 2H), 4.87 (s, 2H), 3.93 (s, 3H), 3.46 (septet, J=7 Hz, 1H), 1.33 (d, J=7 Hz, 6H). ESI LCMS m/z 546 $(M+H)^+$.

10d) 7-[4-({[3-(2,6-dichlorophenyl)-5-(1-methylethyl)-4-isoxazolyl]methyl}oxy)phenyl]-1-naphthalenecarboxylic acid

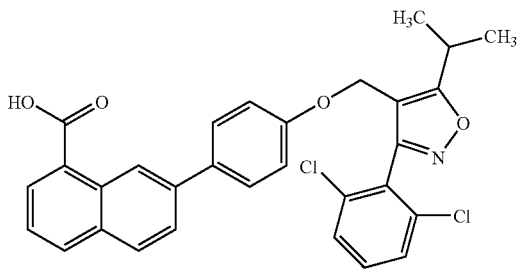

A solution of methyl 7-[4-({[3-(2,6-dichlorophenyl)-5-(1-methylethyl)-4-isoxazolyl]methyl}oxy)phenyl]-1-naphthalenecarboxylate (0.122 g, 0.22 mmol) in THF (2.2 mL) was placed in a microwave reaction tube. Methanol (1.1 mL) was added, followed by 1N sodium hydroxide (0.33 mL, 0.33 mmol). The tube was sealed and heated in a microwave reactor to 100° C. for 600 seconds. The solution was neutralized and concentrated. Water was added and the mixture was filtered. The resulting solid was dried in a vacuum oven at 45° C. with $P_2O_5$ to yield the title compound (0.095 g, 77% as 0.4 tetrahydrofuran) $^1$H NMR (DMSO-$d_6$): δ 13.3-13.1 (broad s, approximately 1H), 9.05 (s, 1H), 8.14-8.12 (m, 2H), 8.04 (d, J=9 Hz, 1H), 7.82-7.79 (m, 1H), 7.63-7.52 (m, 6H), 6.92 (d, J=9 Hz, 2H), 4.87 (s, 2H), 3.46 (septet, J=7 Hz, 1H), 1.33 (d, J=7 Hz, 6H). HRMS $C_{30}H_{23}NO_4Cl_2$ m/z 532.1082 $(M+H)^+_{Cal}$; 532.1074 $(M+H)^+_{Obs}$.

EXAMPLE 11

7-[4-({[3-[2-(2,6-dichlorophenyl)ethyl]-5-(1-methylethyl)-4-isoxazolyl]methyl}oxy)phenyl]-1-naphthalenecarboxylic acid

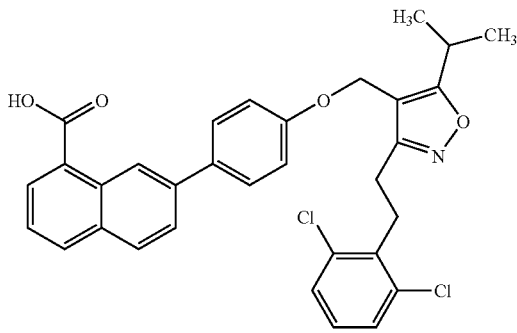

11a) Methyl 7-[4-({[3-[2-(2,6-dichlorophenyl)ethyl]-5-(1-methylethyl)-4-isoxazolyl]methyl}oxy)phenyl]-1-naphthalenecarboxylate

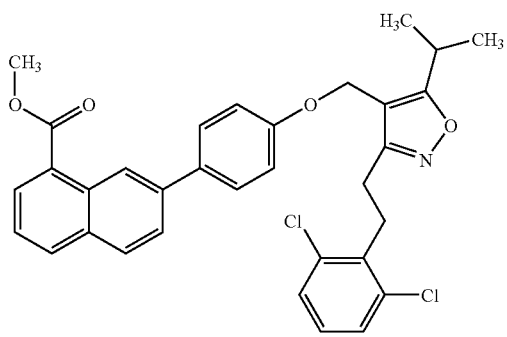

A solution of [3-[2-(2,6-dichlorophenyl)ethyl]-5-(1-methylethyl)-4-isoxazolyl]methanol (0.050 g, 0.16 mmol), methyl 7-(4-hydroxyphenyl)-1-naphthalenecarboxylate (0.045 g, 0.16 mmol), triphenyl phosphine (0.042 g, 0.16 mmol) and diisopropyl azodicarboxylate (0.043 mL, 0.16 mmol) in dichloromethane (1.6 mL) was placed in microwave reaction tube and heated to 80° C. for 20 minutes. The solution was concentrated and the residue was purified by chromatography (silica gel, hexane to 3:7 ethyl acetate:hexanes) to provide the title compound (0.053 g, 58%). $^1$H NMR (DMSO-$d_6$): δ 8.99 (s, 1H), 8.20 (d, J=8 Hz, 1H), 8.16 (d, J=7 Hz, 1H), 8.09 (d, J=9 Hz, 1H), 7.90 (d, J=9 Hz, 1H), 7.74 (d, J=8 Hz, 2H), 7.59-7.56 (m, 1H), 7.41 (d, J=8 Hz, 2H), 7.26-7.24 (m, 1H), 7.16 (d, J=8 Hz, 2H), 4.99 (s, 2H), 3.94 (s, 3H), 3.39-3.20 (2 m, overlapping $H_2O$, total 3H), 2.89-2.85 (m, 2H), 1.25 (d, J=7 Hz, 6H). ESI-LCMS m/z 574 $(M+H)^+$.

11b) 7-[4-({[3-[2-(2,6-dichlorophenyl)ethyl]-5-(1-methylethyl)-4-isoxazolyl]methyl}oxy)phenyl]-1-naphthalenecarboxylic acid

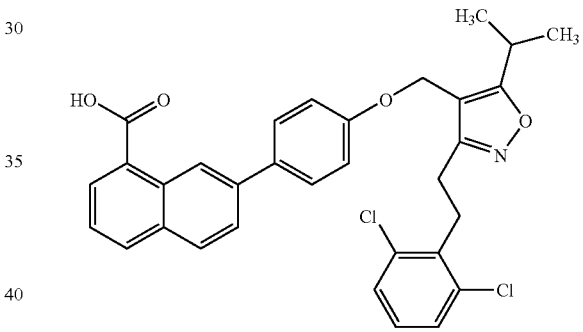

A solution of methyl 7-[4-({[3-[2-(2,6-dichlorophenyl)ethyl]-5-(1-methylethyl)-4-isoxazolyl]methyl}oxy)phenyl]-1-naphthalenecarboxylate (0.052 g, 0.09 mmol) in tetrahydrofuran (0.9 mL) was placed in a microwave reaction tube. Methanol (0.45 mL) was added followed by 1N sodium hydroxide (0.14 mL, 0.14 mmol). The tube was sealed and heated in a microwave reactor to 100° C. for 600 seconds. The solution was neutralized and concentrated. Water was added and the mixture was filtered. The resulting solid was dried in a vacuum oven at 45° C. with $P_2O_5$ to yield the title compound (0.039 g, 74% as 0.40 tetrahydrofuran) $^1$H NMR (DMSO-$d_6$): δ 13.13 (s, 1H), 9.10 (s, 1H), 8.17-8.15 (m, 1H), 8.07 (d, J=9 Hz, 1H) 7.87 (dd, J=2, 9 Hz; 1H), 7.71 (d, J=9 Hz, 2H), 7.57-7.54 (m, 1H), 7.41 (d, J=8 Hz, 2H), 7.28-7.24 (m, J=8 Hz, 2H), 7.16 (dd, J=9, 2 Hz, 2H), 4.98 (s, 2H), 3.36 (septet, overlapping $H_2O$, 1H), 3.23-3.20 (m, 2H), 2.89-2.85 (m, 2H), 1.25 (d, J=7 Hz, 6H). HRMS $C_{32}H_{27}NO_4Cl_2$ m/z 560.1395 $(M+H)^+_{Cal}$; 560.1375 $(M+H)^+_{Obs}$.

EXAMPLE 12

5-{6-[4-({[3-(2,6-dichlorophenyl)-5-(1-methylethyl)-4-isoxazolyl]methyl}oxy)phenyl]-1-naphthalenyl}-1H-tetrazole

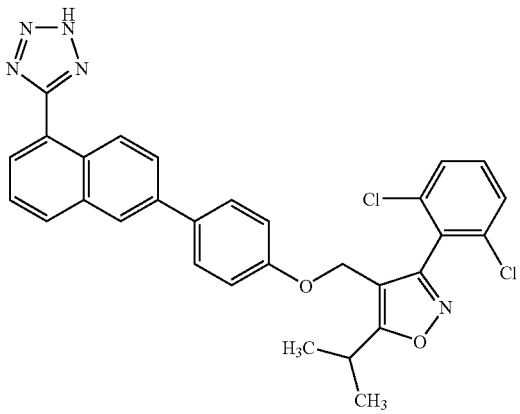

12a) 6-[4-({[3-(2,6-dichlorophenyl)-5-(1-methylethyl)-4-isoxazolyl]methyl}oxy)phenyl]-1-naphthalenecarboxamide

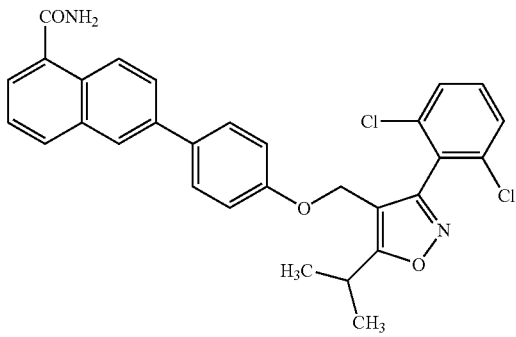

6-[4-({[3-(2,6-dichlorophenyl)-5-(1-methylethyl)-4-isoxazolyl]methyl}oxy)phenyl]-1-naphthalenecarboxylic acid (97 mg, 0.180 mmol), di-tert-butyl dicarbonate (60 mg, 0.273 mmol), and pyridine (0.021 mL, 0.273 mmol) were combined into anhydrous acetonitrile (5 mL). The mixture was stirred at ambient temperature for half an hour. Ammonium hydrogen carbonate (25 mg, 0.273 mmol) was then added to the mixture and the reaction was stirred at ambient temperature for 48 hours. The solvent was then removed on a rotary evaporator and the crude residue was dissolved in ethyl acetate. The organic solution was then washed with water three times, followed by saturated sodium bicarbonate, and then brine. The crude organic extract was then dried over magnesium sulfate, filtered, and then evaporated to dryness. The residue was washed with hexanes several times to remove the residual di-tert-butyl dicarbonate, and the solids were removed via filtration to give the title compound as a white solid (94 mg, 98%) $^1$H NMR (CDCl$_3$): δ 8.48 (d, J=9 Hz, 1H), 7.88-8.00 (m, 2H), 7.75 (d, J=9 Hz, 1H), 7.68 (d, J=9 Hz, 1H), 7.58 (d, J=9 Hz, 2H), 7.36-7.51 (m, 3H) 7.25 (d, J=9 Hz, 1 H), 6.88 (d, J=9 Hz, 2H), 6.42 (broad s, 1H), 6.13 (broad s, 1H), 4.81 (s, 2H), 3.26-3.44 (m, 1H), 1.37-1.47 (m, 6H). ESI-LCMS m/z 531 (M+H)$^+$.

12b) 6-[4-({[3-(2,6-dichlorophenyl)-5-(1-methylethyl)-4-isoxazolyl]methyl}oxy)phenyl]-1-naphthalenecarbonitrile

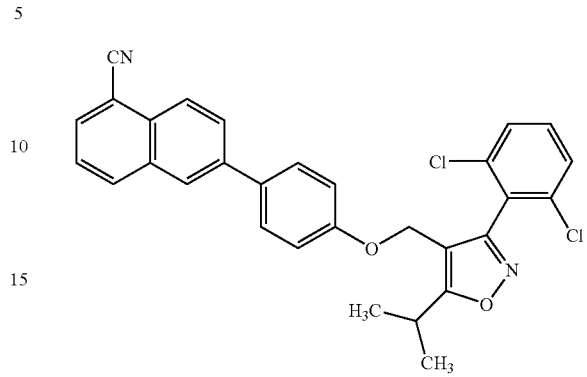

To a solution of 6-[4-({[3-(2,6-dichlorophenyl)-5-(1-methylethyl)-4-isoxazolyl]methyl}oxy)phenyl]-1-naphthalenecarboxamide (94 mg, 0.18 mmol) and triethylamine (0.111 mL, 0.80 mmol) in methylene chloride (2 mL) at ambient temperature under nitrogen was added phosphrous oxychloride (0.068 mL, 0.71 mmol). The mixture was stirred at ambient temperature for four hours, at which time an additional equivalent of phosphorous oxychloride (0.027 mL) was added. Ammonium hydrogen carbonate (25 mg, 0.273 mmol) was then added to the mixture and the reaction was stirred at ambient temperature for 48 hours. The solvent was then removed on a rotary evaporator and the crude residue was dissolved in ethyl acetate. The organic solution was then washed with water three times, followed by saturated sodium bicarbonate, and then brine. The crude organic extract was then dried over magnesium sulfate, filtered, and then evaporated to dryness to give the title compound (89 mg, 98%).
$^1$H NMR (CDCl$_3$): δ 8.24 (d, J=9 Hz, 1H), 8.13 (d, J=9 Hz, 1H), 8.02 (d, J=9 Hz, 1H), 7.82-7.90 (m, 2H), 7.61-7.50 (m, 3H), 7.31-7.52 (m, 3H), 6.88 (d, J=9 Hz, 2H), 4.78 (s, 2H), 3.28-3.42 (m, 1H), 1.34-1.53 (m, 6H). ESI-LCMS m/z 513 (M+H)$^+$.

12c) 5-{6-[4-({[3-(2,6-dichlorophenyl)-5-(1-methylethyl)-4-isoxazolyl]methyl}oxy)phenyl]-1-naphthalenyl}-1H-tetrazole

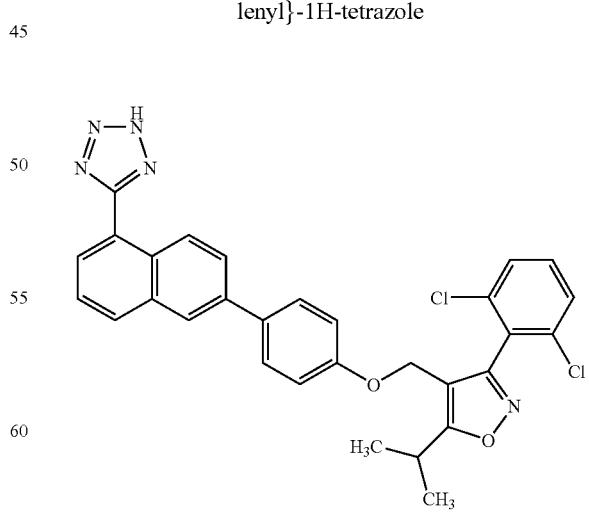

To a solution of 6-[4-({[3-(2,6-dichlorophenyl)-5-(1-methylethyl)-4-isoxazolyl]methyl}oxy)phenyl]-1-naphthalenecarbonitrile (75 mg, 0.14 mmol) in dimethylformamide (1 mL) was added ammonium chloride (8.5 mg, 0.15 mmol) and sodium azide (10 mg, 0.15 mmol). The mixture was then heated to 100° C. for 18 hours. The reaction was diluted with water (5 mL) and acidified with 2 N HCl (2 mL). A white precipitate was formed upon acidification which was removed via filtration and dried under high vacuum for four hours. The crude residue was then dissolved in methanol (5 mL) and purified via preparative high pressure liquid chromatography (C18 Luna column eluted with a 10-100% gradient of acetonitrile in water with 0.1% formic acid modifier) to give the title compound as a white solid (62 mg, 78%) $^1$H NMR (CDCl$_3$): δ 8.54 (d, J=9 Hz, 1H), 7.91-8.02 (m, 2H), 7.75 (d, J=9 Hz, 1H), 7.73 (d, J=9 Hz, 1H), 7.54 (dd, J=2, 8 Hz, 1H), 7.60-7.48 (m, 3H) 7.38 (d, J=9 Hz, 2H), 7.34-7.27 (m, 1H), 6.88 (d, J=9 Hz, 2H), 4.78 (s, 2H), 3.42-3.28 (m, 1H), 1.53-1.34 (m, 6H). ESI-LCMS m/z 556 (M+H)$^+$.

EXAMPLE 13

6-[4-({[3-(2,6-Dichlorophenyl)-5-(1-methylethyl)-4-isoxazolyl]methyl}oxy)phenyl]-1-naphthoic acid tris(hydroxymethyl)aminomethane salt

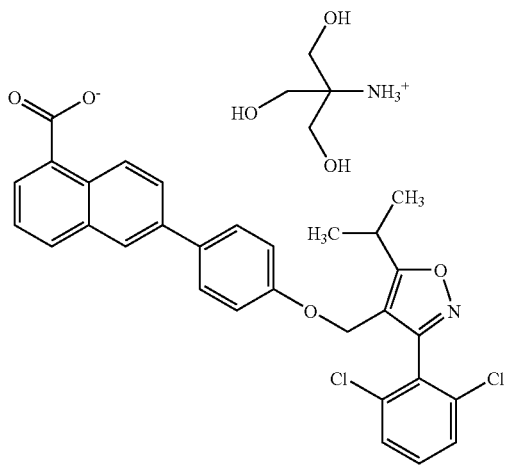

A stirred suspension of 6-[4-({[3-(2,6-dichlorophenyl)-5-(1-methylethyl)-4-isoxazolyl]methyl}oxy)phenyl]-1-naphthalenecarboxylic acid (11.34 g, 0.021 mol) in a solution of 95:5 acetonitrile:water (300 mL) was treated with tris(hydroxymethyl)aminomethane (2.54 g, 0.021 mol). The resulting solution was stirred overnight at 70° C. The mixture was cooled to 5° C. and maintained for 30 minutes. The product was collected by filtration, washed with a solution of 95:5 acetonitrile:water and dried in a vacuum oven at 50° C. with a slow flow of nitrogen to give a crystalline tromethamine salt (13.11 g, 94.34%) of the product. $^1$H NMR (DMSO-d$_6$): δ 9.02 (d, J=10 Hz, 1H), 8.10 (d, J=2 Hz, 1H), 7.94 (d, J=9 Hz, 1H), 7.88 (d, J=7 Hz, 1H), 7.76 (dd, J=2, 9 Hz, 1H), 7.70-7.64 (m, 4H), 7.56 (dd, J=7, 9 Hz, 1H), 7.47 (t, J=8 Hz, 1H), 6.92 (d, J=9 Hz, 2H), 4.89 (s, 2H), 3.53 (s, 6H), 3.48 (septet, J=7 Hz, 1H), 1.35 (d, J=7 Hz, 6H).

BIOLOGICAL EXAMPLE 14

FXR Cofactor Binding Assay

Determination of a ligand mediated cofactor peptide interaction to quantify ligand binding to the nuclear receptor Farnasoid X Receptor (FXR). The method measures the ability of putative ligands to modulate the interaction between the purified bacterial expressed human FXR ligand binding domain (LBD) and a synthetic biotinylated peptide based on residues 676-700 of steroid receptor coactivator-1 (SRC-1) (LXXLL-containing domain-2 where L is the amino acid leucine and X indicates any other amino acid (LCD2), 676-700). The sequence of the SRC-1 peptide used is as published in Iannone, M. A. et al, Cytometry 44:326-337 (2001) where the N-terminus was biotinylated (B) and the C-terminus was amidated. Detection of the associated complex was measured by time resolved fluorescence (TRF). The purified LBD of FXR was labeled with biotin then mixed with stoichiometric amounts of allophycocyanin (APC) labeled streptavidin (Molecular Probes). The biotinylated peptide was then mixed with a ½ stoichiometric amount of europium labeled streptavidin (Wallac Inc). Each was then blocked with a 5 fold excess of biotin and allowed to equilibrate for 15 min. Equimolar amounts of receptor and peptide were mixed together and were allowed to equilibrate for at least 30 min prior to the addition to either a variable or constant concentrations of the sample for which the affinity is to be determined. After equilibration, the time-resolved fluorescent signal was quantitated using a fluorescent plate reader. The affinity of the test compound was estimated from a plot of fluorescence versus concentration of test compound added.

A basal level of FXR: peptide formation is observed in the absence of added ligand. Ligands that promote the complex formation induce a concentration-dependent increase in time-resolved fluorescent signal. Compounds which bind equally well to both non-/un-complexed FXR and to the FXR: peptide complex would be expected to give no change in signal, whereas ligands which bind preferentially to the non-/un-complexed receptor would be expected to induce a concentration-dependent decrease in the observed signal.

Methods & Materials

Advance Preparation: Human Farnasoid X Receptor Ligand Binding Domain

Human FXR Ligand Binding Domain (FXR LBD) was expressed in E. coli strain BL21 (DE3) as an amino-terminal polyhistidine tagged fusion protein. Expression was under the control of an isopropyl-β-D-thiogalactopyranoside (IPTG) inducible T7 promoter. DNA encoding this recombinant protein is subcloned into the pRSET-A expression vector (Invitrogen). The coding sequence of Human FXR LBD was derived from Genbank accession number U 68233 (amino acids 237 to 472).

Ten-liter fermentation batches were grown in Rich PO$_4$ media with 0.1 mg/mL Ampicillin at 25° C. for 12 hours, cooled to 9° C. and held at that temperature for 36 hours to a density of OD$_{600}$=14. At this cell density, 0.25 mM IPTG is added and induction proceeded for 24 hours at 9° C., to a final OD$_{600}$=16. Cells are harvested by centrifugation (20 minutes, 3500× gravity, 4° C.), and concentrated cell slurries were stored in phosphate buffered saline (PBS) at −8° C.

Purification of Receptor Ligand Binding Domain

Routinely, 30-40 g cell paste (equivalent to 2-3 liters of the fermentation batch) was resuspended in 200-250 mL Tris buffered saline (TBS), pH 7.2 (25 mM Tris-Hydroxymethylamino methane (Tris), 150 mM NaCl). Cells were lysed by passing 3 times through a French Press and cell debris was removed by centrifugation (30 minutes, 20,000× gravity, 4° C.). The cleared supernatant was filtered through course pre-filters, and TBS, pH 7.2, 500 mM imidazole was added to obtain a final imidazole concentration of 50 mM. This lysate was loaded onto a column (6×8 cm) packed with Sepharose [Ni$^{++}$ charged] Chelation resin (Pharmacia) and pre-equilibrated with TBS pH 7.2/50 mM imidazole. After washing to baseline absorbance with equilibration buffer, the column was washed with one column volume of TBS pH 7.2 containing 90 mM imidazole. FXR LBD was eluted directly with 365 mM imidazole. Column fractions were pooled and dialyzed against TBS, pH 7.2, containing 0.5 mM EDTA and 5 mM DTT. The dialyzed protein sample was concentrated using Centri-prep 10 K (Amicon) and subjected to size exclusion, using a column (3×90 cm) packed with Sepharose S-75 resin (Pharmacia) pre-equilibrated with TBS, pH 7.2, containing 0.5 mM ethylene diamine tetraacetic acid (EDTA) and 5 mM dithiothreitol (DTT).

Biotinylation of FXR

Purified FXR LBD was desalted/buffer exchanged using PD-10 gel filtration columns into PBS [100 mM $Na_2PO_4$, pH 7.2, 150 mM NaCl]. The concentration of FXR LBD was approximately 20-50 µM in PBS and five-fold molar excess of NHS-LC-Biotin (Pierce) is added in a minimal volume of PBS. This solution was incubated with gentle mixing for 30 minutes at room temperature. The biotinylation modification reaction was stopped by the addition of 2000× molar excess of Tris-HCl, pH 8. The modified FXR LBD was dialyzed against 4 buffer changes, each of at least 50 volumes, PBS containing 5 mM DTT, 2 mM EDTA and 2% sucrose. The biotinylated FXR LBD was then subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

Preparation of Streptavidin-(Europium Chelate)-SRC1:Streptavdin-(APC)—FXR Complex Biotinylated SRC-1(LCD2, 676-700) peptide and a ½ stoichiometric amount of streptavidin-conjugated europium chelate was incubated in assay buffer containing 10 mM DTT for at least 30 minutes. A second solution of stoichiometric amounts of biotinylated FXR and streptavidin-conjugated APC was incubated in assay buffer containing 10 mM DTT for at least 30 minutes. Each solution was then blocked with a 5 fold molar excess of biotin and allowed to equilibrate for at least 30 min. The labeled receptor and cofactor were mixed and again allowed to equilibrate for at least 30 min, added to the compound plate, utilizing e.g., a Titertek Multidrop 384.

Materials:

Assay Buffer: 50 mM 3-(N-morpholino)propanesulfonic acid (MOPS) pH 7.5, 50 mM NaF, 50 µM 3-[(3-cholamidopropyl)-demethylammonio]-1-propanesulfonate (CHAPS), 0.1 mg/ml Fraction 5 fatty acid free bovine serum albumin (BSA). The assay buffer also contained 1 mM ethylenediaminetetraacetic acid (EDTA) for samples run pursuant to the protocol indicated by ¶. Solid DTT is added to the assay buffer to a final concentration of 10 mM just before use in the assay.BSA, fatty acid free
DTT
NaF
Europium labeled Streptavidin: (Wallac CR28-100)
384 well Plates Methods:

Experimental Details:

Test compounds and controls were serial diluted in DMSO and 0.1 µL or 0.5 µL at the desired concentration were added to a 384 well plate.

To each well to be assayed a previously prepared solution of FXR-APC and Europium labeled SRC1 was added to either 0.1 µL of test compound and controls for a final assay volume of 10 µL (indicated by †) or added to 0.5 µL of test compound and controls for a final assay volume of 25 µL (indicated by ◊).

The plates were incubated for at least 1 hour at room temperature and the fluorescent signal determined in a Fluorescence Reader in a time resolved mode utilizing e.g., a Wallac Viewlux Imager or Wallac Victor Multilabel counter.

Data Reduction:

For each concentration of test compound, the results of each test well was expressed as % of control, C, calculated according to eq. 1.

$$C = 100 * \frac{F_{sample} - F_{basal}}{F_{std} - F_{basal}} \qquad (1)$$

where $F_{sample}$ is the signal observed in a particular sample well, $F_{total}$ is the signal observed in the presence of control inhibitor and $F_{basal}$ is the count rate observed in the presence of no ligand. The values used for $F_{std}$ and $F_{basal}$ are averages of the corresponding control wells included on every plate. The results are reported in Table 1 below. In Table 1, + indicates a $pEC_{50}$ of 5-5.99; ++ indicates a $pEC_{50}$ 6-6.99 and +++ indicates a $pEC_{50}$ greater than 7.

TABLE 1

| Example | Activity ($pEC_{50}$) |
| --- | --- |
| 1† | +++ |
| 1◊ | +++ |
| 2† | ++ |
| 3† | ++ |
| 4◊ | ++ |
| 5† | ++ |
| 5◊ | +++ |
| 6† | ++ |
| 7† | ++ |
| 8† | ++ |
| 9† | ++ |
| 10† | + |
| 11† | + |
| 12a◊ | + |
| 12b◊ | + |
| 12c◊ | ++ |

That which is claimed is:

1. A compound of formula (I):

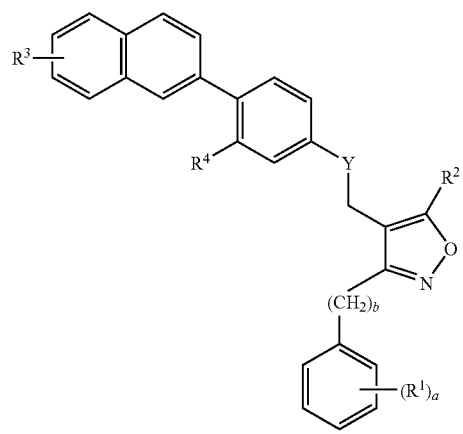

wherein:
a is 1, 2, 3, 4 or 5;
each $R^1$ is the same or different and is independently selected from the group consisting of halo, alkyl, alkenyl, —O—$CF_3$, —$OR^6$, —$S(O)_jR^6$, —$NR^6R^7$, —$R^5OR^6$, —$R^5S(O)_jR^6$, —$R^5NR^6R^7$ and cyano;
b is 0, 1, 2 or 3;
$R^2$ is selected from the group consisting of alkyl, alkenyl, $C_{3-6}$cycloalkyl, $C_{3-6}$cycloalkenyl, —$R^5OR^6$, —$R^5NR^6R^7$ and cyano;

Y is —O—, —S— or —N(R$^8$)—;

R$^3$ is an acid, amide, ester or acid-equivalent group;

R$^4$ is H, halo, alkyl or haloalkyl;

each R$^5$ is the same or different and is independently selected from the group consisting of alkylene and alkenylene;

each R$^6$ and R$^7$ are the same or different and are each independently selected from the group consisting of H, alkyl, alkenyl, C$_{3-6}$cycloalkyl and C$_{3-6}$cyclolalkenyl; and f is 0, 1 or 2;

each R$^8$ is the same or different and is independently H or alkyl;

or a pharmaceutically acceptable salt thereof.

2. The compound according to claim 1 wherein a is 1 or 2.

3. The compound according to claim 1 wherein each R$^1$ is the same or different and is independently selected from the group consisting of halo or —OR$^6$.

4. The compound according to claim 1 wherein each R$^1$ is the same or different and is independently halo.

5. The compound according to claim 1 where b is 0 or 2.

6. The compound according to claim 1 where b is 0.

7. The compound according to claim 1 where R$^2$ is selected from the group consisting of alkyl or C$_{3-6}$cycloalkyl.

8. The compound according to claim 1 where Y is —O—.

9. The compound according to claim 1 where R$^3$ is an acid.

10. The compound according to claim 1 where R$^4$ is H.

11. A compound selected from the group consisting of:

6-[4-({[3-(2,6-dichlorophenyl)-5-(1-methylethyl)-4-isoxazolyl]methyl}oxy)phenyl]-1-naphthoic acid sodium salt;

6-[4-({[3-(2,6-dichlorophenyl)-5-(1-methylethyl)-4-isoxazolyl]methyl}oxy)phenyl]-1-naphthalenecarboxylic acid;

6-[2-Chloro-4-({[3-(2,6-dichlorophenyl)-5-(1-methylethyl)-4-isoxazolyl]methyl}oxy)phenyl]-1-naphthalenecarboxylic acid;

6-[4-({[5-cyclobutyl-3-(2,6-dichlorophenyl)-4-isoxazolyl]methyl}oxy)phenyl]-1-naphthalenecarboxylic acid;

6-[4-({[3-[(2,6-dichlorophenyl)methyl]-5-(1-methylethyl)-4-isoxazolyl]methyl}oxy)phenyl]-1-naphthalenecarboxylic acid;

6-[4-({[3-[2-(2,6-dichlorophenyl)ethyl]-5-(1-methylethyl)-4-isoxazolyl]methyl}oxy)phenyl]-1-naphthalenecarboxylic acid;

6-(4-{[3-(2,6-dichlorophenyl)-5-isopropylisoxazol-4-yl]methoxy}phenyl)-2-naphthoic acid;

Methyl 6-[4-({[3-[2-(2,6-dichlorophenyl)ethyl]-5-(1-methylethyl)-4-isoxazolyl]methyl}oxy)phenyl]-2-naphthalenecarboxylate;

7-[4-({[3-(2,6-dichlorophenyl)-5-(1-methylethyl)-4-isoxazolyl]methyl}oxy)phenyl]-2-naphthalenecarboxylic acid;

7-[4-({[3-[2-(2,6-dichlorophenyl)ethyl]-5-(1-methylethyl)-4-isoxazolyl]methyl}oxy)phenyl]-2-naphthalenecarboxylic acid;

7-[4-({[3-(2,6-dichlorophenyl)-5-(1-methylethyl)-4-isoxazolyl]methyl}oxy)phenyl]-1-naphthalenecarboxylic acid;

7-[4-({[3-[2-(2,6-dichlorophenyl)ethyl]-5-(1-methylethyl)-4-isoxazolyl]methyl}oxy)phenyl]-1-naphthalenecarboxylic acid;

6-[4-({[3-(2,6-dichlorophenyl)-5-(1-methylethyl)-4-isoxazolyl]methyl}oxy)phenyl]-1-naphthalenecarboxamide;

6-[4-({[3-(2,6-dichlorophenyl)-5-(1-methylethyl)-4-isoxazolyl]methyl}oxy)phenyl]-1-naphthalenecarbonitrile;

5-{6-[4-({[3-(2,6-dichlorophenyl)-5-(1-methylethyl)-4-isoxazolyl]methyl}oxy)phenyl]-1-naphthalenyl}-1H-tetrazole; and 6-[4-({[3-(2,6-dichlorophenyl)-5-(1-methylethyl)-4-isoxazolyl]methyl}oxy)phenyl]-1-naphthoic acid tris(hydroxymethyl)aminomethane salt.

12. 6-[4-({[3-(2,6-Dichlorophenyl)-5-(1-methylethyl)-4-isoxazolyl]methyl}oxy)phenyl]-1-naphthalenecarboxylic acid or a pharmaceutically acceptable salt thereof.

13. 6-[4-({[3-(2,6-Dichlorophenyl)-5-(1-methylethyl)-4-isoxazolyl]methyl}oxy)phenyl]-1-naphthoic acid tris(hydroxymethyl)aminomethane salt.

14. A pharmaceutical composition comprising a compound according to claims 1 and a pharmaceutically acceptable carrier.

15. A pharmaceutical composition comprising 6-[4-({[3-(2,6-Dichlorophenyl)-5-(1-methylethyl)-4-isoxazolyl]methyl}oxy)phenyl]-1-naphthalenecarboxylic acid or a pharmaceutically acceptable salt or solvate thereof and a pharmaceutically acceptable carrier.

16. A pharmaceutical composition comprising 6-[4-({[3-(2,6-Dichlorophenyl)-5-(1-methylethyl)-4-isoxazolyl]methyl}oxy)phenyl]-1-naphthoic acid tris (hydroxymethyl)aminomethane salt and a pharmaceutically acceptable carrier.

17. A process for preparing a compound according to any of claims 1-13 comprising the steps of:

a) reacting a compound of formula (VIII)

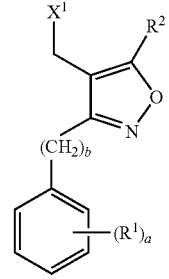

VIII with a compound of formula (IX)

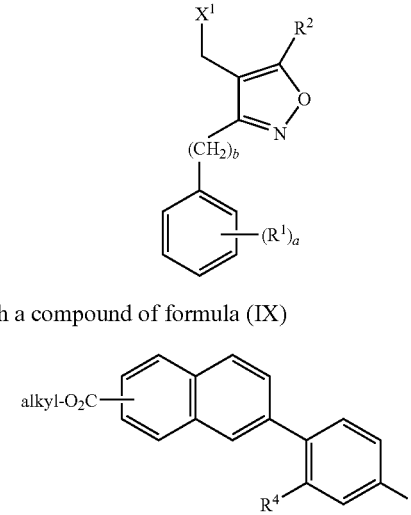

IX to prepare a compound of formula (I-A);

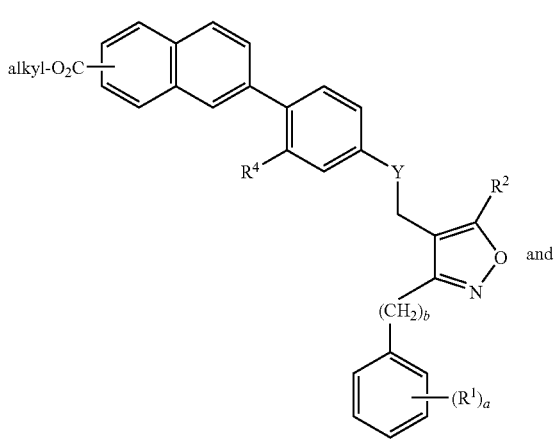

I-A and b) optionally converting the compound of formula (I-A) into a different compound of formula (I).

18. A process for preparing a compound according to any of claims 1-13 comprising the steps of:

a) reacting a compound of formula (VIII-B)

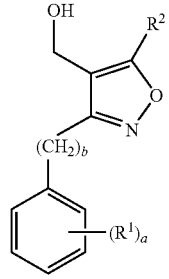

with a compound of formula (IX)

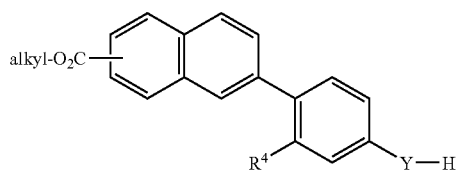

to prepare a compound of formula (I-A);

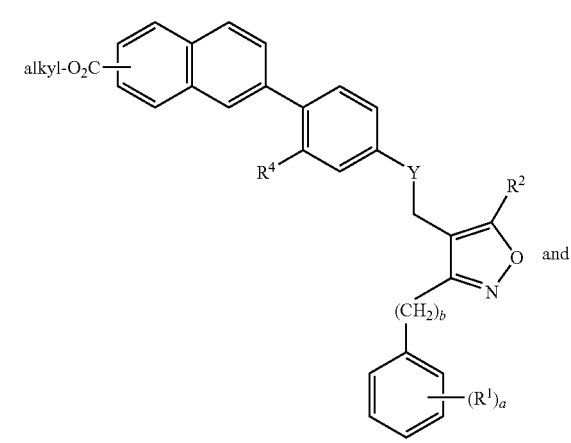

b) optionally converting the compound of formula (I-A) into a different compound of formula (I).

* * * * *